United States Patent
Stanely et al.

(10) Patent No.: US 9,671,391 B2
(45) Date of Patent: Jun. 6, 2017

(54) IL-34 RECEPTOR ASSAYS AND USES THEREOF

(71) Applicant: ALBERT EINSTEIN COLLEGE OF MEDICINE, INC., Bronx, NY (US)

(72) Inventors: Evan Richard Stanely, New York, NY (US); Sayan Nandi, Bronx, NY (US); Yee-Guide Yeung, Hartsdale, NY (US)

(73) Assignee: ALBERT EINSTEIN COLLEGE OF MEDICINE, INC., Bronx, NY (US)

( * ) Notice: Subject to any disclaimer, the term of this patent is extended or adjusted under 35 U.S.C. 154(b) by 0 days.

(21) Appl. No.: 14/891,405

(22) PCT Filed: May 19, 2014

(86) PCT No.: PCT/US2014/038590
§ 371 (c)(1),
(2) Date: Nov. 16, 2015

(87) PCT Pub. No.: WO2014/189832
PCT Pub. Date: Nov. 27, 2014

(65) Prior Publication Data
US 2016/0123962 A1    May 5, 2016

Related U.S. Application Data

(60) Provisional application No. 61/826,356, filed on May 22, 2013.

(51) Int. Cl.
*G01N 33/50* (2006.01)
*C07K 16/24* (2006.01)

(52) U.S. Cl.
CPC ....... *G01N 33/5058* (2013.01); *C07K 16/244* (2013.01); *G01N 33/5011* (2013.01); *G01N 2333/916* (2013.01)

(58) Field of Classification Search
None
See application file for complete search history.

(56) References Cited

U.S. PATENT DOCUMENTS
2010/0130527 A1    5/2010 Lehrer et al.

FOREIGN PATENT DOCUMENTS
WO    2013011021 A1    1/2013

OTHER PUBLICATIONS

PCT International Search Report and Written Opinion, dated Oct. 1, 2014 in connection with PCT International Application No. PCT/US2014/38590, 10 pages.
Nakamichi Y et al., entitled "Spleen serves as a reservoir of osteoclast precursors through vitamin D-induced IL-34 expression in osteopetrotic op/op mice," PNAS, Jun. 19, 2012, vol. 109, No. 25, pp. 10006-10011.
Ulbricht U et al., entitled "RNA interference targeting protein tyrosine phosphatase zeta/receptor-type protein tyrosine phosphatase beta suppresses glioblastoma growth in vitro and in vivo," Journal of Neurochemistry, 2006, 98, 1497-1506.
Maeda N et al., entitled "A Receptor-like Protein-tyrosine Phosphatase PTP zeta/RPTPbeta Binds a Heparin-binding Growth Factor Midkine: Involvement of Arginine 78 of Midkine in the High Affinity Binding to PTPz," J. Biol. Chem. 1999, 274:12474-12479.
Nandi S et al., entitled "Receptor-type Protein-tyrosine Phosphatase zeta is a Functional Receptor for Interleukin-34," Biol. Chem. 2013, 288:21972-21986.

*Primary Examiner* — Daniel E Kolker
*Assistant Examiner* — Aditi Dutt
(74) *Attorney, Agent, or Firm* — Amster, Rothstein & Ebenstein LLP

(57) ABSTRACT

Methods are disclosed for identifying activators and inhibitors of actions of interleukin-34 (IL-34) that are independent of the colony stimulating factor-1 (CSF-1) receptor (CSF-1R) and play a role in development, homeostasis and disease.

9 Claims, 8 Drawing Sheets

FIGURE 7A-7B

SEQUENCE LISTING

<160> NUMBER OF SEQ ID NOS: 12

<210> SEQ ID NO 1
<211> LENGTH: 57
<212> TYPE: DNA
<213> ORGANISM: Artificial
<220> FEATURE:
<223> OTHER INFORMATION: PTP-zeta hairpin sequence

<400> SEQUENCE: 1
gatccccaga tttctaccac aacattcaag agatgttgtg gtagaaatct ggttttt    57

```
<210> SEQ ID NO 2
<211> LENGTH: 21
<212> TYPE: DNA
<213> ORGANISM: Artificial
<220> FEATURE:
<223> OTHER INFORMATION: sense siRNA sequence

<400> SEQUENCE: 2
ccagauuucu accacaacat t                                              21

<210> SEQ ID NO 3
<211> LENGTH: 21
<212> TYPE: DNA
<213> ORGANISM: Artificial
<220> FEATURE:
<223> OTHER INFORMATION: antisense siRNA sequence

<400> SEQUENCE: 3
uguuguggua gaaaucuggt t                                              21

<210> SEQ ID NO 4
<211> LENGTH: 57
<212> TYPE: DNA
<213> ORGANISM: Artificial
<220> FEATURE:
<223> OTHER INFORMATION: hairpin sequence

<400> SEQUENCE: 4 gatcccncaca gagatggttc tgtattcaag agatacagaa ccatctctgt ggttttt      57

<210> SEQ ID NO 5
<211> LENGTH: 21
<212> TYPE: DNA
<213> ORGANISM: Artificial
<220> FEATURE:
<223> OTHER INFORMATION: sense siRNA sequence

<400> SEQUENCE: 5
ccacagagau gguucuguat t                                              21

<210> SEQ ID NO 6
<211> LENGTH: 21
<212> TYPE: DNA
<213> ORGANISM: Artificial
<220> FEATURE:
<223> OTHER INFORMATION: antisense siRNA sequence

<400> SEQUENCE: 6
uacagaacca ucucuguggt t                                              21

<210> SEQ ID NO 7
<211> LENGTH: 57
<212> TYPE: DNA
<213> ORGANISM: Artificial
<220> FEATURE:
<223> OTHER INFORMATION: hairpin sequence

<400> SEQUENCE: 7
gatcccgaag gaactgtcaa catattcaag agatatgttg acagttcctt cgttttt       57

<210> SEQ ID NO 8
<211> LENGTH: 21
<212> TYPE: DNA
<213> ORGANISM: Artificial
<220> FEATURE:
<223> OTHER INFORMATION: sense siRNA sequence
```

<400> SEQUENCE: 8
cgaaggaacu gucaacauat t                                              21

<210> SEQ ID NO 9
<211> LENGTH: 21
<212> TYPE: DNA
<213> ORGANISM: Artificial
<220> FEATURE:
<223> OTHER INFORMATION: antisense siRNA sequence

<400> SEQUENCE: 9
uauguugaca guccuucgt t                                               21

<210> SEQ ID NO 10
<211> LENGTH: 1250
<212> TYPE: PRT
<213> ORGANISM: Mus musculus

<400> SEQUENCE: 10

Met Gly Ile Asp Gly Glu Thr Val Val Leu Lys Asn Met Leu Ile Gly
1               5                   10                  15

Val Asn Leu Ile Leu Leu Gly Ser Met Leu Lys Pro Ser Glu Cys Arg
            20                  25                  30

Leu Glu Val Leu Gln Glu Leu Leu Ser Arg Ile Glu Met Leu Glu Arg
        35                  40                  45

Glu Val Ser Leu Leu Arg Asp Gln Cys Asn Thr Asn Cys Cys Gln Glu
    50                  55                  60

Ser Ala Ala Thr Gly Gln Leu Asp Tyr Val Pro His Cys Ser Gly His
65                  70                  75                  80

Gly Asn Phe Ser Phe Glu Ser Cys Gly Cys Ile Cys Asn Glu Gly Trp
                85                  90                  95

Phe Gly Lys Asn Cys Ser Glu Pro Tyr Cys Pro Leu Gly Cys Ser Ser
            100                 105                 110

Arg Gly Val Cys Val Asp Gly Gln Cys Ile Cys Asp Ser Glu Tyr Ser
        115                 120                 125

Gly Asp Asp Cys Ser Glu Leu Arg Cys Pro Thr Asp Cys Ser Ser Arg
    130                 135                 140

Gly Leu Cys Val Asp Gly Glu Cys Val Cys Glu Glu Pro Tyr Thr Gly
145                 150                 155                 160

Glu Asp Cys Arg Glu Leu Arg Cys Pro Gly Asp Cys Ser Gly Lys Gly
                165                 170                 175

Gln Cys Ala Asn Gly Thr Cys Leu Cys Gln Glu Gly Tyr Ala Gly Glu
            180                 185                 190

Asp Cys Ser Gln Arg Arg Cys Leu Asn Ala Cys Ser Gly Arg Gly His
        195                 200                 205

Cys Gln Glu Gly Leu Cys Ile Cys Glu Glu Gly Tyr Gln Gly Pro Asp
    210                 215                 220

Cys Ser Ala Val Ala Pro Glu Asp Leu Arg Val Ala Gly Ile Ser
225                 230                 235                 240

Asp Arg Ser Ile Glu Leu Glu Trp Asp Gly Pro Met Ala Val Thr Glu
                245                 250                 255

Tyr Val Ile Ser Tyr Gln Pro Thr Ala Leu Gly Gly Leu Gln Leu Gln
            260                 265                 270

Gln Arg Val Pro Gly Asp Trp Ser Gly Val Thr Ile Thr Glu Leu Glu
        275                 280                 285

-continued

```
Pro Gly Leu Thr Tyr Asn Ile Ser Val Tyr Ala Val Ile Ser Asn Ile
290                 295                 300

Leu Ser Leu Pro Ile Thr Ala Lys Val Ala Thr His Leu Ser Thr Pro
305                 310                 315                 320

Gln Gly Leu Gln Phe Lys Thr Ile Thr Glu Thr Thr Val Glu Val Gln
                325                 330                 335

Trp Glu Pro Phe Ser Phe Ser Phe Asp Gly Trp Glu Ile Ser Phe Ile
                340                 345                 350

Pro Lys Asn Asn Glu Gly Gly Val Ile Ala Gln Leu Pro Ser Asp Val
                355                 360                 365

Thr Ser Phe Asn Gln Thr Gly Leu Lys Pro Gly Glu Glu Tyr Ile Val
370                 375                 380

Asn Val Val Ala Leu Lys Glu Gln Ala Arg Ser Pro Pro Thr Ser Ala
385                 390                 395                 400

Ser Val Ser Thr Val Ile Asp Gly Pro Thr Gln Ile Leu Val Arg Asp
                405                 410                 415

Val Ser Asp Thr Val Ala Phe Val Glu Trp Thr Pro Pro Arg Ala Lys
                420                 425                 430

Val Asp Phe Ile Leu Leu Lys Tyr Gly Leu Val Gly Gly Glu Gly Gly
                435                 440                 445

Lys Thr Thr Phe Arg Leu Gln Pro Pro Leu Ser Gln Tyr Ser Val Gln
450                 455                 460

Ala Leu Arg Pro Gly Ser Arg Tyr Glu Val Ser Ile Ser Ala Val Arg
465                 470                 475                 480

Gly Thr Asn Glu Ser Glu Ala Ser Ser Thr Gln Phe Thr Thr Glu Ile
                485                 490                 495

Asp Ala Pro Lys Asn Leu Arg Val Gly Ser Arg Thr Ala Thr Ser Leu
                500                 505                 510

Asp Leu Glu Trp Asp Asn Ser Glu Ala Glu Ala Gln Glu Tyr Lys Val
                515                 520                 525

Val Tyr Ser Thr Leu Ala Gly Glu Gln Tyr His Glu Val Leu Val Pro
                530                 535                 540

Lys Gly Ile Gly Pro Thr Thr Lys Thr Thr Leu Thr Asp Leu Val Pro
545                 550                 555                 560

Gly Thr Glu Tyr Gly Val Gly Ile Ser Ala Val Met Asn Ser Lys Gln
                565                 570                 575

Ser Ile Pro Ala Thr Met Asn Ala Arg Thr Glu Leu Asp Ser Pro Arg
                580                 585                 590

Asp Leu Met Val Thr Ala Ser Ser Glu Thr Ser Ile Ser Leu Ile Trp
                595                 600                 605

Thr Lys Ala Ser Gly Pro Ile Asp His Tyr Arg Ile Thr Phe Thr Pro
610                 615                 620

Ser Ser Gly Ile Ser Ser Glu Val Thr Val Pro Arg Asp Arg Thr Ser
625                 630                 635                 640

Tyr Thr Leu Thr Asp Leu Glu Pro Gly Ala Glu Tyr Ile Ile Ser Ile
                645                 650                 655

Thr Ala Glu Arg Gly Arg Gln Gln Ser Leu Glu Ser Thr Val Asp Ala
                660                 665                 670

Phe Thr Gly Phe Arg Pro Ile Ser His Leu His Phe Ser His Val Thr
                675                 680                 685

Ser Ser Ser Val Asn Ile Thr Trp Ser Asp Ser Pro Pro Ala Asp
690                 695                 700

Arg Leu Ile Leu Asn Tyr Ser Pro Arg Asp Lys Glu Glu Asp Met Leu
```

```
                705                 710                 715                 720
            Glu Val Leu Leu Asp Ala Thr Lys Arg His Ala Val Leu Met Gly Leu
                            725                 730                 735
            Gln Pro Ala Thr Glu Tyr Ile Val Asn Leu Ala Val His Gly Thr
                            740                 745                 750
            Val Thr Ser Glu Pro Ile Val Gly Ser Ile Thr Thr Gly Ile Asp Pro
                            755                 760                 765
            Pro Lys Asn Ile Thr Ile Ser Asn Val Thr Lys Asp Ser Leu Thr Val
                770                 775                 780
            Ser Trp Ser Ser Pro Val Ala Pro Phe Asp Tyr Tyr Arg Val Ser Tyr
            785                 790                 795                 800
            Arg Pro Thr Gln Val Gly Arg Leu Asp Ser Ser Val Val Pro Asn Thr
                            805                 810                 815
            Val Thr Glu Phe Ala Ile Thr Arg Leu Tyr Pro Ala Thr Glu Tyr Glu
                            820                 825                 830
            Ile Ser Leu Asn Ser Val Arg Gly Arg Glu Glu Ser Glu Arg Ile Cys
                            835                 840                 845
            Thr Leu Val His Thr Ala Met Asp Ser Pro Met Asp Leu Ile Ala Thr
                            850                 855                 860
            Asn Ile Thr Pro Thr Glu Ala Leu Leu Gln Trp Lys Ala Pro Met Gly
            865                 870                 875                 880
            Glu Val Glu Asn Tyr Val Ile Val Leu Thr His Phe Ala Ile Ala Gly
                            885                 890                 895
            Glu Thr Ile Leu Val Asp Gly Val Ser Glu Glu Phe Gln Leu Val Asp
                            900                 905                 910
            Leu Leu Pro Ser Thr His Tyr Thr Val Thr Met Tyr Ala Thr Ser Gly
                            915                 920                 925
            Pro Leu Met Ser Gly Thr Ile Ala Thr Asn Phe Ser Thr Leu Leu Asp
                            930                 935                 940
            Pro Pro Asp Asn Leu Thr Ala Ser Glu Val Thr Arg Gln Ser Ala Leu
            945                 950                 955                 960
            Ile Ser Trp Gln Pro Pro Arg Ala Ala Ile Glu Asn Tyr Val Leu Thr
                            965                 970                 975
            Tyr Lys Ser Thr Asp Gly Ser Arg Lys Glu Leu Ile Val Asp Ala Glu
                            980                 985                 990
            Asp Thr Trp Ile Arg Leu Glu Gly Leu Ser Glu Asn Thr Asp Tyr Thr
                            995                1000                1005
            Val Leu Leu Gln Ala Ala Gln Glu Ala Thr Arg Ser Ser Leu Thr
                        1010                1015                1020
            Ser Thr Val Phe Thr Thr Gly Gly Arg Val Phe Ser His Pro Gln
                        1025                1030                1035
            Asp Cys Ala Gln His Leu Met Asn Gly Asp Thr Leu Ser Gly Val
                        1040                1045                1050
            Tyr Thr Ile Phe Leu Asn Gly Glu Leu Ser His Lys Leu Gln Val
                        1055                1060                1065
            Tyr Cys Asp Met Thr Thr Asp Gly Gly Gly Trp Ile Val Phe Gln
                        1070                1075                1080
            Arg Arg Gln Asn Gly Gln Thr Asp Phe Phe Arg Lys Trp Ala Asp
                        1085                1090                1095
            Tyr Arg Val Gly Phe Gly Asn Leu Glu Asp Glu Phe Trp Leu Gly
                        1100                1105                1110
            Leu Asp Asn Ile His Arg Ile Thr Ala Gln Gly Arg Tyr Glu Leu
                        1115                1120                1125
```

```
Arg Val Asp Met Arg Asp Gly Gln Glu Ala Val Phe Ala Tyr Tyr
    1130              1135                1140

Asp Lys Phe Ala Val Glu Asp Ser Arg Ser Leu Tyr Lys Ile Arg
    1145              1150                1155

Ile Gly Ser Tyr Asn Gly Thr Ala Gly Asp Ser Leu Ser Tyr His
    1160              1165                1170

Gln Gly Arg Pro Phe Ser Thr Glu Asp Arg Asp Asn Asp Val Ala
    1175              1180                1185

Val Thr Asn Cys Ala Met Ser Tyr Lys Gly Ala Trp Trp Tyr Lys
    1190              1195                1200

Asn Cys His Arg Thr Asn Leu Asn Gly Lys Tyr Gly Glu Ser Arg
    1205              1210                1215

His Ser Gln Gly Ile Asn Trp Tyr His Trp Lys Gly His Glu Phe
    1220              1225                1230

Ser Ile Pro Phe Val Glu Met Lys Met Arg Pro Tyr Ile His Arg
    1235              1240                1245

Leu Thr
    1250

<210> SEQ ID NO 11
<211> LENGTH: 2312
<212> TYPE: PRT
<213> ORGANISM: Mus musculus

<400> SEQUENCE: 11

Met Arg Ile Leu Gln Ser Phe Leu Ala Cys Val Gln Leu Leu Cys Leu
1               5                   10                  15

Cys Arg Leu Asp Trp Ala Tyr Gly Tyr Tyr Arg Gln Gln Arg Lys Leu
                20                  25                  30

Val Glu Glu Ile Gly Trp Ser Tyr Thr Gly Ala Leu Asn Gln Lys Asn
            35                  40                  45

Trp Gly Lys Lys Tyr Pro Ile Cys Asn Ser Pro Lys Gln Ser Pro Ile
    50                  55                  60

Asn Ile Asp Glu Asp Leu Thr Gln Val Asn Val Asn Leu Lys Lys Leu
65                  70                  75                  80

Lys Phe Gln Gly Trp Glu Lys Ala Ser Leu Glu Asn Thr Phe Ile His
                85                  90                  95

Asn Thr Gly Lys Thr Val Glu Ile Asn Leu Thr Asn Asp Tyr Tyr Leu
                100                 105                 110

Ser Gly Gly Leu Ser Glu Lys Val Phe Lys Ala Ser Lys Ile Thr Phe
            115                 120                 125

His Trp Gly Lys Cys Asn Val Ser Ser Glu Gly Ser Glu His Ser Leu
    130                 135                 140

Glu Gly Gln Lys Phe Pro Leu Glu Met Gln Val Tyr Cys Phe Asp Ala
145                 150                 155                 160

Asp Arg Phe Ser Ser Phe Glu Glu Ala Val Lys Gly Lys Gly Arg Leu
                165                 170                 175

Arg Ala Leu Ser Ile Leu Phe Glu Val Gly Val Glu Glu Asn Leu Asp
            180                 185                 190

Tyr Lys Ala Ile Ile Asp Gly Thr Glu Ser Val Ser Arg Phe Gly Lys
        195                 200                 205

Gln Ala Ala Leu Asp Pro Phe Val Leu Gln Asn Leu Leu Pro Asn Ser
    210                 215                 220

Thr Asp Lys Tyr Tyr Ile Tyr Asn Gly Ser Leu Thr Ser Pro Pro Cys
```

```
            225                 230                 235                 240
        Thr Asp Thr Val Glu Trp Ile Val Phe Lys Asp Thr Val Ser Ile Ser
                            245                 250                 255
        Glu Ser Gln Leu Ala Val Phe Cys Glu Val Leu Thr Met Gln Gln Ser
                        260                 265                 270
        Gly Tyr Val Met Leu Met Asp Tyr Leu Gln Asn Asn Phe Arg Glu Gln
                        275                 280                 285
        Gln Tyr Lys Phe Ser Arg Gln Val Phe Ser Ser Tyr Thr Gly Lys Glu
                    290                 295                 300
        Glu Ile His Glu Val Val Cys Ser Ser Glu Pro Glu Asn Val Gln Ala
        305                 310                 315                 320
        Asp Pro Glu Asn Tyr Thr Ser Leu Leu Val Thr Trp Glu Arg Pro Arg
                            325                 330                 335
        Val Val Tyr Asp Ala Met Ile Glu Lys Phe Ala Val Leu Tyr Gln Pro
                        340                 345                 350
        Leu Ala Gly Asn Asp Gln Ala Lys His Glu Phe Leu Thr Asp Gly Tyr
                        355                 360                 365
        Gln Asp Leu Gly Ala Ile Leu Asn Asn Leu Leu Pro Asn Met Ser Tyr
                    370                 375                 380
        Val Leu Gln Ile Val Ala Val Cys Ser Asn Gly Leu Tyr Gly Lys Tyr
        385                 390                 395                 400
        Ser Asp Gln Leu Ile Val Asp Met Pro Thr Glu Asp Ala Glu Leu Asp
                            405                 410                 415
        Leu Phe Pro Glu Leu Ile Gly Thr Glu Glu Ile Ile Lys Glu Glu Glu
                        420                 425                 430
        Tyr Gly Lys Asp Asn Glu Glu Asp Thr Gly Leu Asn Pro Gly Arg Asp
                        435                 440                 445
        Ser Val Thr Asn Gln Ile Arg Lys Lys Glu Pro Gln Val Ser Thr Thr
                    450                 455                 460
        Thr His Tyr Asn His Met Gly Thr Lys Tyr Asn Glu Ala Lys Thr Asn
        465                 470                 475                 480
        Arg Ser Pro Thr Arg Gly Ser Glu Phe Ser Gly Lys Ser Asp Val Pro
                            485                 490                 495
        Asn Thr Ser Pro Asn Ser Thr Ser Gln His Val Ala Glu Phe Glu Thr
                        500                 505                 510
        Glu Arg Gly Ile Ser Leu Pro Ser Gln Thr Gly Thr Asn Leu Pro Pro
                        515                 520                 525
        His Asn Val Glu Gly Thr Ser Ala Ser Leu Asn Ser Gly Ser Lys Thr
                    530                 535                 540
        Leu Phe Ile Phe Pro Gln Met Asn Leu Ser Gly Thr Ala Glu Ser Leu
        545                 550                 555                 560
        Asn Thr Val Pro Ile Thr Glu Tyr Lys Glu Val Ser Ala Asp Val Ser
                            565                 570                 575
        Glu Glu Glu Asn Phe Leu Thr Asp Phe Lys Leu Asp Thr Gly Ala Asp
                        580                 585                 590
        Asp Ser Ser Gly Ser Ser Pro Ser Thr Ser Val Pro Phe Ser Ser
                        595                 600                 605
        Asp Asn Leu Ser His Gly Tyr Ile Thr Ser Asp Met Pro Glu Ala
                    610                 615                 620
        Ile Thr Tyr Asp Val Leu Lys Pro Gly Ser Thr Arg Asn Ala Pro Glu
        625                 630                 635                 640
        Asp Ser Ala Pro Ser Gly Ser Glu Glu Ser Leu Lys Asp Pro Ser Leu
                            645                 650                 655
```

-continued

```
Glu Gly Ser Val Trp Phe Pro Gly Ser Thr Asp Leu Thr Thr Gln Ser
            660                 665                 670

Glu Thr Gly Ser Gly Arg Glu Ser Phe Leu Gln Val Asn Ser Thr Asp
            675                 680                 685

Ile Gln Ile Asp Glu Ser Arg Glu Thr Thr Glu Ser Phe Ser Pro Asp
690                 695                 700

Ala Thr Val Ser Gln Asp Pro Ser Val Thr Asp Met Gly Met Pro His
705                 710                 715                 720

Tyr Ser Thr Phe Ala Tyr Leu Pro Thr Glu Val Thr Pro Gln Ala Phe
                725                 730                 735

Thr Pro Ser Ser Arg Pro Leu Asp Leu Ala Pro Thr Ile Asn Ile Leu
            740                 745                 750

His Ser Gln Thr Thr Gln Pro Val Tyr Asn Gly Glu Thr Pro Leu Gln
            755                 760                 765

Pro Ser Tyr Ser Ser Glu Val Phe Pro Leu Ala Thr Pro Leu Leu Leu
            770                 775                 780

Asp Asn Gln Thr Leu Asn Thr Thr Pro Ala Ala Ser Ser Ser Asp Ser
785                 790                 795                 800

Ala Leu His Ala Thr Pro Val Ser Pro Ser Val Gly Val Ser Phe Glu
                805                 810                 815

Ser Ile Leu Ser Ser Tyr Asp Asp Ala Pro Leu Leu Pro Phe Ser Ser
            820                 825                 830

Ala Ser Phe Ser Ser Glu Met Phe Arg His Leu His Thr Val Ser Gln
            835                 840                 845

Thr Leu Pro Gln Val Thr Ser Ala Ala Glu Arg Asp Glu Leu Ser Leu
850                 855                 860

His Ala Ser Leu Leu Val Ala Arg Gly Asp Leu Leu Leu Glu Pro Ser
865                 870                 875                 880

Leu Val Gln Tyr Ser Asp Val Ala Ser His Gln Ala Thr Thr Arg Ala
                885                 890                 895

Ala Ser Asp Thr Leu Gly Phe Gly Ser Glu Ser Ala Val Phe Tyr Lys
            900                 905                 910

Thr Ser Met Val Ser Gln Ile Glu Ser Pro Arg Ser Asp Val Val Met
            915                 920                 925

His Ala Tyr Ser Ser Gly Pro Glu Pro Ser Tyr Thr Val Glu Gly Ser
            930                 935                 940

His His Val Pro Thr Val Ser Tyr Ser Ser Ala Met Pro Leu His Gly
945                 950                 955                 960

Ser Val Asp Val Ser Asp Gln Gly Ser Leu Leu Ile Asn Pro Ser His
                965                 970                 975

Ile Ser Met Pro Glu Ser Ser Phe Ile Thr Pro Thr Ala Ser Leu Leu
            980                 985                 990

Gln Pro Pro Pro Ala Leu Ser Gly Asp Gly Glu Trp Ser Gly Ala Ser
            995                 1000                1005

Ser Asp Ser Glu Leu Leu Leu Pro Asp Ala Asp Gly Leu Arg Thr
        1010                1015                1020

Leu Asn Ile Ser Ser Pro Val Ser Val Ala Glu Phe Thr Tyr Thr
        1025                1030                1035

Thr Ser Val Phe Ala Asp Gly Ile Lys Pro Leu Ser Lys Ser Glu
        1040                1045                1050

Met Met Tyr Gly Asn Glu Thr Glu Leu Lys Met Ser Ser Phe Ser
        1055                1060                1065
```

```
Asp Met Ala Tyr Pro Ser Lys Ser Thr Val Val Pro Lys Met Ser
    1070            1075            1080

Asp Val Val His Lys Trp Ser Glu Ser Leu Lys Glu Thr Ser Val
    1085            1090            1095

Ser Ile Ser Ser Met Lys Ser Val Phe Pro Glu Ser Leu Val Tyr
    1100            1105            1110

Pro Thr Thr Lys Gly Phe Glu Gln Gly Val Ser His Val Pro Glu
    1115            1120            1125

Ile Ile Phe Pro Val Gln Pro Thr His Thr Ala Ser Gln Ala Ser
    1130            1135            1140

Gly Asp Thr Trp Leu Lys Pro Gly Leu Ser Ala Asn Ser Glu Ala
    1145            1150            1155

Ala Phe Ser Asp Thr Ala Ser Arg Glu Val Val His Pro Ser Thr
    1160            1165            1170

Gln Pro Leu Leu Tyr Glu Ala Ala Thr Pro Phe Asn Thr Glu Ala
    1175            1180            1185

Leu Leu Gln Pro Ser Phe Gln Ala Ser Asp Val Asp Thr Leu Leu
    1190            1195            1200

Lys Thr Ala Leu Pro Ser Val Pro Ser Asp Pro Ile Leu Ala Gly
    1205            1210            1215

Thr Pro Gln Val Glu Gln Ser Ser Ser Val Ser His Pro Met
    1220            1225            1230

Ala Ser Glu Ser Gly Ser Ser Glu Ser Met Leu His Phe Thr Ser
    1235            1240            1245

Val Pro Ile Leu Asp Ile Ser Pro Ser Lys Val His Ser Thr Pro
    1250            1255            1260

Leu Gln Gly Leu Thr Val Pro His Ser Ser Lys Lys Phe Ser Glu
    1265            1270            1275

Gln Gly Leu Leu Lys Ser Lys Ser Pro Gln Gln Val Leu Pro Ser
    1280            1285            1290

Leu Phe Ser Asn Asp Glu Phe Phe Gln Ser Ala His Leu Asp Val
    1295            1300            1305

Ser Gln Ala Tyr Pro Pro Lys Gly Arg His Ala Phe Val Thr Pro
    1310            1315            1320

Val Leu Ser Ile Asp Glu Pro Gln Asn Thr Leu Ile Asn Lys Leu
    1325            1330            1335

Val Tyr Ser Glu Asp Ile Phe Ser Ser Thr Glu Ile Ser Ile Thr
    1340            1345            1350

Asp Lys Val Leu Thr Gly Leu Pro Thr Leu Ala Ser Asp Val Leu
    1355            1360            1365

Ser Ser Thr Asp His Ser Val Pro Leu Gly Ser Gly Pro Ile Ser
    1370            1375            1380

Leu Thr Met Val Ser Pro Asn Arg Asp Asp Ser Val Thr Thr Ala
    1385            1390            1395

Lys Leu Leu Leu Pro Ser Thr Ala Thr Ser Lys Leu Thr Gln Ser
    1400            1405            1410

Ala Arg Ser Asp Ala Asp Leu Val Gly Gly Gly Glu Asp Gly Asp
    1415            1420            1425

Asp Tyr Asp Asp Asp Asp Tyr Asp Asp Ile Asp Arg Gly Arg Phe
    1430            1435            1440

Pro Val Asn Lys Cys Met Ser Cys Leu Pro Tyr Arg Glu Ser Arg
    1445            1450            1455

Glu Lys Val Met Asn Asp Ser Asp Thr Gln Glu Ser Ser Leu Val
```

-continued

```
            1460                1465                1470
Asp Gln Ser Asp Pro Ile Ser Pro Leu Leu Phe Glu Asn Thr Glu
        1475                1480                1485
Glu Glu Asn Gly Gly Thr Gly Val Thr Arg Val Asp Lys Ser Pro
        1490                1495                1500
Pro Pro Ser Met Leu Pro Gln Asn His Asn Asp Gly Lys Glu Asp
        1505                1510                1515
Ser Asp Ile Gln Met Gly Ser Ala Val Leu Pro His Thr Pro Gly
        1520                1525                1530
Ser Lys Ala Trp Ala Val Leu Thr Ser Asp Glu Glu Ser Gly Ser
        1535                1540                1545
Gly Gln Gly Thr Ser Asp Ser Leu Asn Asp Asn Glu Thr Ser Thr
        1550                1555                1560
Asp Phe Ser Phe Pro Asp Val Asn Glu Lys Asp Thr Asp Gly Val
        1565                1570                1575
Leu Glu Thr Asp Asp Thr Gly Ile Ala Pro Gly Ser Pro Arg Ser
        1580                1585                1590
Ser Thr Pro Ser Val Thr Ser Gly His Ser Gly Val Ser Asn Ser
        1595                1600                1605
Ser Glu Ala Glu Ala Ser Asn Ser Ser His Glu Ser Arg Ile Gly
        1610                1615                1620
Leu Ala Glu Gly Leu Glu Ser Glu Lys Lys Ala Val Ile Pro Leu
        1625                1630                1635
Val Ile Val Ser Ala Leu Thr Phe Ile Cys Leu Val Val Leu Val
        1640                1645                1650
Gly Ile Leu Ile Tyr Trp Arg Lys Cys Phe Gln Thr Ala His Phe
        1655                1660                1665
Tyr Leu Glu Asp Asn Thr Ser Pro Arg Val Ile Ser Thr Pro Pro
        1670                1675                1680
Thr Pro Ile Phe Pro Ile Ser Asp Asp Ile Gly Ala Ile Pro Ile
        1685                1690                1695
Lys His Phe Pro Lys His Val Ala Asp Leu His Ala Ser Asn Gly
        1700                1705                1710
Phe Thr Glu Glu Phe Glu Thr Leu Lys Glu Phe Tyr Gln Glu Val
        1715                1720                1725
Gln Ser Cys Thr Ala Asp Leu Gly Ile Thr Ala Asp Ser Ser Asn
        1730                1735                1740
His Pro Asp Asn Lys His Lys Asn Arg Tyr Val Asn Ile Val Ala
        1745                1750                1755
Tyr Asp His Ser Arg Val Lys Leu Thr Gln Leu Ala Glu Lys Asp
        1760                1765                1770
Gly Lys Leu Thr Asp Tyr Ile Asn Ala Asn Tyr Val Asp Gly Tyr
        1775                1780                1785
Asn Arg Pro Lys Ala Tyr Ile Ala Ala Gln Gly Pro Leu Lys Ser
        1790                1795                1800
Thr Ala Glu Asp Phe Trp Arg Met Ile Trp Glu His Asn Val Glu
        1805                1810                1815
Val Ile Val Met Ile Thr Asn Leu Val Glu Lys Gly Arg Arg Lys
        1820                1825                1830
Cys Asp Gln Tyr Trp Pro Thr Asp Gly Ser Glu Glu Tyr Gly Ser
        1835                1840                1845
Phe Leu Val Asn Gln Lys Ser Val Gln Val Leu Ala Tyr Tyr Thr
        1850                1855                1860
```

-continued

Val Arg Asn Phe Thr Leu Arg Asn Thr Lys Leu Lys Lys Gly Ser
1865                 1870                 1875

Gln Lys Gly Arg Ser Ser Gly Arg Leu Val Thr Gln Tyr His Tyr
1880                 1885                 1890

Thr Gln Trp Pro Asp Met Gly Val Pro Glu Tyr Ser Leu Pro Val
1895                 1900                 1905

Leu Ala Phe Val Arg Lys Ala Ala Gln Ala Lys Arg His Ala Val
1910                 1915                 1920

Gly Pro Val Val Val His Cys Ser Ala Gly Val Gly Arg Thr Gly
1925                 1930                 1935

Thr Tyr Ile Val Leu Asp Ser Met Leu Gln Gln Ile Gln His Glu
1940                 1945                 1950

Gly Thr Val Asn Ile Phe Gly Phe Leu Lys His Ile Arg Ser Gln
1955                 1960                 1965

Arg Asn Tyr Leu Val Gln Thr Glu Gln Tyr Val Phe Ile His
1970                 1975                 1980

Asp Thr Leu Val Glu Ala Ile Leu Ser Lys Glu Thr Glu Val Pro
1985                 1990                 1995

Asp Ser His Ile His Ser Tyr Val Asn Thr Leu Leu Ile Pro Gly
2000                 2005                 2010

Pro Thr Gly Lys Thr Lys Leu Glu Lys Gln Phe Gln Leu Leu Ser
2015                 2020                 2025

Gln Ser Asn Ile Leu Gln Ser Asp Tyr Ser Thr Ala Leu Lys Gln
2030                 2035                 2040

Cys Asn Arg Glu Lys Asn Arg Thr Ser Ser Ile Ile Pro Val Glu
2045                 2050                 2055

Arg Ser Arg Val Gly Ile Ser Ser Leu Ser Gly Glu Gly Thr Asp
2060                 2065                 2070

Tyr Ile Asn Ala Ser Tyr Ile Met Gly Tyr Tyr Gln Ser Asn Glu
2075                 2080                 2085

Phe Ile Ile Thr Gln His Pro Leu Leu His Thr Ile Lys Asp Phe
2090                 2095                 2100

Trp Arg Met Ile Trp Asp His Asn Ala Gln Leu Val Val Met Ile
2105                 2110                 2115

Pro Asp Gly Gln Asn Met Ala Glu Asp Glu Phe Val Tyr Trp Pro
2120                 2125                 2130

Asn Lys Asp Glu Pro Ile Asn Cys Glu Ser Phe Lys Val Thr Leu
2135                 2140                 2145

Met Ser Glu Glu His Lys Cys Leu Ser Asn Glu Glu Lys Leu Ile
2150                 2155                 2160

Val Gln Asp Phe Ile Leu Glu Ala Thr Gln Asp Asp Tyr Val Leu
2165                 2170                 2175

Glu Val Arg His Phe Gln Cys Pro Lys Trp Pro Asn Pro Asp Ser
2180                 2185                 2190

Pro Ile Ser Lys Thr Phe Glu Leu Ile Ser Ile Ile Lys Glu Glu
2195                 2200                 2205

Ala Ala Asn Arg Asp Gly Pro Met Ile Val His Asp Glu His Gly
2210                 2215                 2220

Gly Val Thr Ala Gly Thr Phe Cys Ala Leu Thr Thr Leu Met His
2225                 2230                 2235

Gln Leu Glu Lys Glu Asn Ala Met Asp Val Tyr Gln Val Ala Lys
2240                 2245                 2250

```
Met Ile Asn Leu Met Arg Pro Gly Val Phe Thr Asp Ile Glu Gln
    2255                2260                2265

Tyr Gln Phe Leu Tyr Lys Val Val Leu Ser Leu Val Ser Thr Arg
    2270                2275                2280

Gln Glu Glu Asn Pro Ser Thr Ser Leu Asp Ser Asn Gly Ala Ala
    2285                2290                2295

Leu Pro Asp Gly Asn Ile Ala Glu Ser Leu Glu Ser Leu Val
    2300                2305                2310

<210> SEQ ID NO 12
<211> LENGTH: 2315
<212> TYPE: PRT
<213> ORGANISM: Homo sapiens

<400> SEQUENCE: 12

Met Arg Ile Leu Lys Arg Phe Leu Ala Cys Ile Gln Leu Leu Cys Val
1               5                   10                  15

Cys Arg Leu Asp Trp Ala Asn Gly Tyr Tyr Arg Gln Arg Lys Leu
            20                  25                  30

Val Glu Glu Ile Gly Trp Ser Tyr Thr Gly Ala Leu Asn Gln Lys Asn
            35                  40                  45

Trp Gly Lys Lys Tyr Pro Thr Cys Asn Ser Pro Lys Gln Ser Pro Ile
50                  55                  60

Asn Ile Asp Glu Asp Leu Thr Gln Val Asn Val Asn Leu Lys Lys Leu
65                  70                  75                  80

Lys Phe Gln Gly Trp Asp Lys Thr Ser Leu Glu Asn Thr Phe Ile His
            85                  90                  95

Asn Thr Gly Lys Thr Val Glu Ile Asn Leu Thr Asn Asp Tyr Arg Val
            100                 105                 110

Ser Gly Gly Val Ser Glu Met Val Phe Lys Ala Ser Lys Ile Thr Phe
            115                 120                 125

His Trp Gly Lys Cys Asn Met Ser Ser Asp Gly Ser Glu His Ser Leu
            130                 135                 140

Glu Gly Gln Lys Phe Pro Leu Glu Met Gln Ile Tyr Cys Phe Asp Ala
145                 150                 155                 160

Asp Arg Phe Ser Ser Phe Glu Glu Ala Val Lys Gly Lys Gly Lys Leu
            165                 170                 175

Arg Ala Leu Ser Ile Leu Phe Glu Val Gly Thr Glu Glu Asn Leu Asp
            180                 185                 190

Phe Lys Ala Ile Ile Asp Gly Val Glu Ser Val Ser Arg Phe Gly Lys
            195                 200                 205

Gln Ala Ala Leu Asp Pro Phe Ile Leu Leu Asn Leu Leu Pro Asn Ser
            210                 215                 220

Thr Asp Lys Tyr Tyr Ile Tyr Asn Gly Ser Leu Thr Ser Pro Pro Cys
225                 230                 235                 240

Thr Asp Thr Val Asp Trp Ile Val Phe Lys Asp Thr Val Ser Ile Ser
            245                 250                 255

Glu Ser Gln Leu Ala Val Phe Cys Glu Val Leu Thr Met Gln Gln Ser
            260                 265                 270

Gly Tyr Val Met Leu Met Asp Tyr Leu Gln Asn Asn Phe Arg Glu Gln
            275                 280                 285

Gln Tyr Lys Phe Ser Arg Gln Val Phe Ser Ser Tyr Thr Gly Lys Glu
            290                 295                 300

Glu Ile His Glu Ala Val Cys Ser Ser Glu Pro Glu Asn Val Gln Ala
305                 310                 315                 320
```

```
Asp Pro Glu Asn Tyr Thr Ser Leu Leu Val Thr Trp Glu Arg Pro Arg
            325                 330                 335

Val Val Tyr Asp Thr Met Ile Glu Lys Phe Ala Val Leu Tyr Gln Gln
            340                 345                 350

Leu Asp Gly Glu Asp Gln Thr Lys His Glu Phe Leu Thr Asp Gly Tyr
            355                 360                 365

Gln Asp Leu Gly Ala Ile Leu Asn Asn Leu Leu Pro Asn Met Ser Tyr
            370                 375                 380

Val Leu Gln Ile Val Ala Ile Cys Thr Asn Gly Leu Tyr Gly Lys Tyr
385                 390                 395                 400

Ser Asp Gln Leu Ile Val Asp Met Pro Thr Asp Asn Pro Glu Leu Asp
                405                 410                 415

Leu Phe Pro Glu Leu Ile Gly Thr Glu Glu Ile Ile Lys Glu Glu
            420                 425                 430

Glu Gly Lys Asp Ile Glu Glu Gly Ala Ile Val Asn Pro Gly Arg Asp
            435                 440                 445

Ser Ala Thr Asn Gln Ile Arg Lys Lys Glu Pro Gln Ile Ser Thr Thr
            450                 455                 460

Thr His Tyr Asn Arg Ile Gly Thr Lys Tyr Asn Glu Ala Lys Thr Asn
465                 470                 475                 480

Arg Ser Pro Thr Arg Gly Ser Glu Phe Ser Gly Lys Gly Asp Val Pro
                485                 490                 495

Asn Thr Ser Leu Asn Ser Thr Ser Gln Pro Val Thr Lys Leu Ala Thr
            500                 505                 510

Glu Lys Asp Ile Ser Leu Thr Ser Gln Thr Val Thr Glu Leu Pro Pro
            515                 520                 525

His Thr Val Glu Gly Thr Ser Ala Ser Leu Asn Asp Gly Ser Lys Thr
            530                 535                 540

Val Leu Arg Ser Pro His Met Asn Leu Ser Gly Thr Ala Glu Ser Leu
545                 550                 555                 560

Asn Thr Val Ser Ile Thr Glu Tyr Glu Glu Glu Ser Leu Leu Thr Ser
                565                 570                 575

Phe Lys Leu Asp Thr Gly Ala Glu Asp Ser Ser Gly Ser Ser Pro Ala
            580                 585                 590

Thr Ser Ala Ile Pro Phe Ile Ser Glu Asn Ile Ser Gln Gly Tyr Ile
            595                 600                 605

Phe Ser Ser Glu Asn Pro Glu Thr Ile Thr Tyr Asp Val Leu Ile Pro
            610                 615                 620

Glu Ser Ala Arg Asn Ala Ser Glu Asp Ser Thr Ser Ser Gly Ser Glu
625                 630                 635                 640

Glu Ser Leu Lys Asp Pro Ser Met Glu Gly Asn Val Trp Phe Pro Ser
                645                 650                 655

Ser Thr Asp Ile Thr Ala Gln Pro Asp Val Gly Ser Gly Arg Glu Ser
            660                 665                 670

Phe Leu Gln Thr Asn Tyr Thr Glu Ile Arg Val Asp Glu Ser Glu Lys
            675                 680                 685

Thr Thr Lys Ser Phe Ser Ala Gly Pro Val Met Ser Gln Gly Pro Ser
            690                 695                 700

Val Thr Asp Leu Glu Met Pro His Tyr Ser Thr Phe Ala Tyr Phe Pro
705                 710                 715                 720

Thr Glu Val Thr Pro His Ala Phe Thr Pro Ser Ser Arg Gln Gln Asp
                725                 730                 735
```

-continued

Leu Val Ser Thr Val Asn Val Val Tyr Ser Gln Thr Gln Pro Val
                740                 745                 750

Tyr Asn Gly Glu Thr Pro Leu Gln Pro Ser Tyr Ser Ser Glu Val Phe
            755                 760                 765

Pro Leu Val Thr Pro Leu Leu Leu Asp Asn Gln Ile Leu Asn Thr Thr
        770                 775                 780

Pro Ala Ala Ser Ser Ser Asp Ser Ala Leu His Ala Thr Pro Val Phe
785                 790                 795                 800

Pro Ser Val Asp Val Ser Phe Glu Ser Ile Leu Ser Ser Tyr Asp Gly
                805                 810                 815

Ala Pro Leu Leu Pro Phe Ser Ser Ala Ser Phe Ser Ser Glu Leu Phe
            820                 825                 830

Arg His Leu His Thr Val Ser Gln Ile Leu Pro Gln Val Thr Ser Ala
        835                 840                 845

Thr Glu Ser Asp Lys Val Pro Leu His Ala Ser Leu Pro Val Ala Gly
        850                 855                 860

Gly Asp Leu Leu Leu Glu Pro Ser Leu Ala Gln Tyr Ser Asp Val Leu
865                 870                 875                 880

Ser Thr Thr His Ala Ala Ser Glu Thr Leu Glu Phe Gly Ser Glu Ser
                885                 890                 895

Gly Val Leu Tyr Lys Thr Leu Met Phe Ser Gln Val Glu Pro Pro Ser
            900                 905                 910

Ser Asp Ala Met Met His Ala Arg Ser Ser Gly Pro Glu Pro Ser Tyr
        915                 920                 925

Ala Leu Ser Asp Asn Glu Gly Ser Gln His Ile Phe Thr Val Ser Tyr
        930                 935                 940

Ser Ser Ala Ile Pro Val His Asp Ser Val Gly Val Thr Tyr Gln Gly
945                 950                 955                 960

Ser Leu Phe Ser Gly Pro Ser His Ile Pro Ile Pro Lys Ser Ser Leu
                965                 970                 975

Ile Thr Pro Thr Ala Ser Leu Leu Gln Pro Thr His Ala Leu Ser Gly
            980                 985                 990

Asp Gly Glu Trp Ser Gly Ala Ser Ser Asp Ser Glu Phe Leu Leu Pro
        995                 1000                1005

Asp Thr Asp Gly Leu Thr Ala Leu Asn Ile Ser Ser Pro Val Ser
        1010                1015                1020

Val Ala Glu Phe Thr Tyr Thr Thr Ser Val Phe Gly Asp Asp Asn
        1025                1030                1035

Lys Ala Leu Ser Lys Ser Glu Ile Ile Tyr Gly Asn Glu Thr Glu
        1040                1045                1050

Leu Gln Ile Pro Ser Phe Asn Glu Met Val Tyr Pro Ser Glu Ser
        1055                1060                1065

Thr Val Met Pro Asn Met Tyr Asp Asn Val Asn Lys Leu Asn Ala
        1070                1075                1080

Ser Leu Gln Glu Thr Ser Val Ser Ile Ser Ser Thr Lys Gly Met
        1085                1090                1095

Phe Pro Gly Ser Leu Ala His Thr Thr Thr Lys Val Phe Asp His
        1100                1105                1110

Glu Ile Ser Gln Val Pro Glu Asn Asn Phe Ser Val Gln Pro Thr
        1115                1120                1125

His Thr Val Ser Gln Ala Ser Gly Asp Thr Ser Leu Lys Pro Val
        1130                1135                1140

Leu Ser Ala Asn Ser Glu Pro Ala Ser Ser Asp Pro Ala Ser Ser

```
            1145                1150                1155
Glu Met Leu Ser Pro Ser Thr Gln Leu Leu Phe Tyr Glu Thr Ser
        1160                1165                1170
Ala Ser Phe Ser Thr Glu Val Leu Leu Gln Pro Ser Phe Gln Ala
        1175                1180                1185
Ser Asp Val Asp Thr Leu Leu Lys Thr Val Leu Pro Ala Val Pro
        1190                1195                1200
Ser Asp Pro Ile Leu Val Glu Thr Pro Lys Val Asp Lys Ile Ser
        1205                1210                1215
Ser Thr Met Leu His Leu Ile Val Ser Asn Ser Ala Ser Ser Glu
        1220                1225                1230
Asn Met Leu His Ser Thr Ser Val Pro Val Phe Asp Val Ser Pro
        1235                1240                1245
Thr Ser His Met His Ser Ala Ser Leu Gln Gly Leu Thr Ile Ser
        1250                1255                1260
Tyr Ala Ser Glu Lys Tyr Glu Pro Val Leu Leu Lys Ser Glu Ser
        1265                1270                1275
Ser His Gln Val Val Pro Ser Leu Tyr Ser Asn Asp Glu Leu Phe
        1280                1285                1290
Gln Thr Ala Asn Leu Glu Ile Asn Gln Ala His Pro Pro Lys Gly
        1295                1300                1305
Arg His Val Phe Ala Thr Pro Val Leu Ser Ile Asp Glu Pro Leu
        1310                1315                1320
Asn Thr Leu Ile Asn Lys Leu Ile His Ser Asp Glu Ile Leu Thr
        1325                1330                1335
Ser Thr Lys Ser Ser Val Thr Gly Lys Val Phe Ala Gly Ile Pro
        1340                1345                1350
Thr Val Ala Ser Asp Thr Phe Val Ser Thr Asp His Ser Val Pro
        1355                1360                1365
Ile Gly Asn Gly His Val Ala Ile Thr Ala Val Ser Pro His Arg
        1370                1375                1380
Asp Gly Ser Val Thr Ser Thr Lys Leu Leu Phe Pro Ser Lys Ala
        1385                1390                1395
Thr Ser Glu Leu Ser His Ser Ala Lys Ser Asp Ala Gly Leu Val
        1400                1405                1410
Gly Gly Gly Glu Asp Gly Asp Thr Asp Asp Asp Gly Asp Asp Asp
        1415                1420                1425
Asp Asp Asp Arg Gly Ser Asp Gly Leu Ser Ile His Lys Cys Met
        1430                1435                1440
Ser Cys Ser Ser Tyr Arg Glu Ser Gln Glu Lys Val Met Asn Asp
        1445                1450                1455
Ser Asp Thr His Glu Asn Ser Leu Met Asp Gln Asn Asn Pro Ile
        1460                1465                1470
Ser Tyr Ser Leu Ser Glu Asn Ser Glu Glu Asp Asn Arg Val Thr
        1475                1480                1485
Ser Val Ser Ser Asp Ser Gln Thr Gly Met Asp Arg Ser Pro Gly
        1490                1495                1500
Lys Ser Pro Ser Ala Asn Gly Leu Ser Gln Lys His Asn Asp Gly
        1505                1510                1515
Lys Glu Glu Asn Asp Ile Gln Thr Gly Ser Ala Leu Leu Pro Leu
        1520                1525                1530
Ser Pro Glu Ser Lys Ala Trp Ala Val Leu Thr Ser Asp Glu Glu
        1535                1540                1545
```

-continued

Ser Gly Ser Gly Gln Gly Thr Ser Asp Ser Leu Asn Glu Asn Glu
    1550                1555                1560

Thr Ser Thr Asp Phe Ser Phe Ala Asp Thr Asn Glu Lys Asp Ala
    1565                1570                1575

Asp Gly Ile Leu Ala Ala Gly Asp Ser Glu Ile Thr Pro Gly Phe
    1580                1585                1590

Pro Gln Ser Pro Thr Ser Ser Val Thr Ser Glu Asn Ser Glu Val
    1595                1600                1605

Phe His Val Ser Glu Ala Glu Ala Ser Asn Ser Ser His Glu Ser
    1610                1615                1620

Arg Ile Gly Leu Ala Glu Gly Leu Glu Ser Glu Lys Lys Ala Val
    1625                1630                1635

Ile Pro Leu Val Ile Val Ser Ala Leu Thr Phe Ile Cys Leu Val
    1640                1645                1650

Val Leu Val Gly Ile Leu Ile Tyr Trp Arg Lys Cys Phe Gln Thr
    1655                1660                1665

Ala His Phe Tyr Leu Glu Asp Ser Thr Ser Pro Arg Val Ile Ser
    1670                1675                1680

Thr Pro Pro Thr Pro Ile Phe Pro Ile Ser Asp Asp Val Gly Ala
    1685                1690                1695

Ile Pro Ile Lys His Phe Pro Lys His Val Ala Asp Leu His Ala
    1700                1705                1710

Ser Ser Gly Phe Thr Glu Glu Phe Glu Thr Leu Lys Glu Phe Tyr
    1715                1720                1725

Gln Glu Val Gln Ser Cys Thr Val Asp Leu Gly Ile Thr Ala Asp
    1730                1735                1740

Ser Ser Asn His Pro Asp Asn Lys His Lys Asn Arg Tyr Ile Asn
    1745                1750                1755

Ile Val Ala Tyr Asp His Ser Arg Val Lys Leu Ala Gln Leu Ala
    1760                1765                1770

Glu Lys Asp Gly Lys Leu Thr Asp Tyr Ile Asn Ala Asn Tyr Val
    1775                1780                1785

Asp Gly Tyr Asn Arg Pro Lys Ala Tyr Ile Ala Ala Gln Gly Pro
    1790                1795                1800

Leu Lys Ser Thr Ala Glu Asp Phe Trp Arg Met Ile Trp Glu His
    1805                1810                1815

Asn Val Glu Val Ile Val Met Ile Thr Asn Leu Val Glu Lys Gly
    1820                1825                1830

Arg Arg Lys Cys Asp Gln Tyr Trp Pro Ala Asp Gly Ser Glu Glu
    1835                1840                1845

Tyr Gly Asn Phe Leu Val Thr Gln Lys Ser Val Gln Val Leu Ala
    1850                1855                1860

Tyr Tyr Thr Val Arg Asn Phe Thr Leu Arg Asn Thr Lys Ile Lys
    1865                1870                1875

Lys Gly Ser Gln Lys Gly Arg Pro Ser Gly Arg Val Val Thr Gln
    1880                1885                1890

Tyr His Tyr Thr Gln Trp Pro Asp Met Gly Val Pro Glu Tyr Ser
    1895                1900                1905

Leu Pro Val Leu Thr Phe Val Arg Lys Ala Ala Tyr Ala Lys Arg
    1910                1915                1920

His Ala Val Gly Pro Val Val Val His Cys Ser Ala Gly Val Gly
    1925                1930                1935

-continued

```
Arg Thr Gly Thr Tyr Ile Val Leu Asp Ser Met Leu Gln Gln Ile
1940                1945                1950

Gln His Glu Gly Thr Val Asn Ile Phe Gly Phe Leu Lys His Ile
1955                1960                1965

Arg Ser Gln Arg Asn Tyr Leu Val Gln Thr Glu Gln Tyr Val
1970                1975                1980

Phe Ile His Asp Thr Leu Val Glu Ala Ile Leu Ser Lys Glu Thr
1985                1990                1995

Glu Val Leu Asp Ser His Ile His Ala Tyr Val Asn Ala Leu Leu
2000                2005                2010

Ile Pro Gly Pro Ala Gly Lys Thr Lys Leu Glu Lys Gln Phe Gln
2015                2020                2025

Leu Leu Ser Gln Ser Asn Ile Gln Gln Ser Asp Tyr Ser Ala Ala
2030                2035                2040

Leu Lys Gln Cys Asn Arg Glu Lys Asn Arg Thr Ser Ser Ile Ile
2045                2050                2055

Pro Val Glu Arg Ser Arg Val Gly Ile Ser Ser Leu Ser Gly Glu
2060                2065                2070

Gly Thr Asp Tyr Ile Asn Ala Ser Tyr Ile Met Gly Tyr Tyr Gln
2075                2080                2085

Ser Asn Glu Phe Ile Ile Thr Gln His Pro Leu Leu His Thr Ile
2090                2095                2100

Lys Asp Phe Trp Arg Met Ile Trp Asp His Asn Ala Gln Leu Val
2105                2110                2115

Val Met Ile Pro Asp Gly Gln Asn Met Ala Glu Asp Glu Phe Val
2120                2125                2130

Tyr Trp Pro Asn Lys Asp Glu Pro Ile Asn Cys Glu Ser Phe Lys
2135                2140                2145

Val Thr Leu Met Ala Glu Glu His Lys Cys Leu Ser Asn Glu Glu
2150                2155                2160

Lys Leu Ile Ile Gln Asp Phe Ile Leu Glu Ala Thr Gln Asp Asp
2165                2170                2175

Tyr Val Leu Glu Val Arg His Phe Gln Cys Pro Lys Trp Pro Asn
2180                2185                2190

Pro Asp Ser Pro Ile Ser Lys Thr Phe Glu Leu Ile Ser Val Ile
2195                2200                2205

Lys Glu Glu Ala Ala Asn Arg Asp Gly Pro Met Ile Val His Asp
2210                2215                2220

Glu His Gly Gly Val Thr Ala Gly Thr Phe Cys Ala Leu Thr Thr
2225                2230                2235

Leu Met His Gln Leu Glu Lys Glu Asn Ser Val Asp Val Tyr Gln
2240                2245                2250

Val Ala Lys Met Ile Asn Leu Met Arg Pro Gly Val Phe Ala Asp
2255                2260                2265

Ile Glu Gln Tyr Gln Phe Leu Tyr Lys Val Ile Leu Ser Leu Val
2270                2275                2280

Ser Thr Arg Gln Glu Glu Asn Pro Ser Thr Ser Leu Asp Ser Asn
2285                2290                2295

Gly Ala Ala Leu Pro Asp Gly Asn Ile Ala Glu Ser Leu Glu Ser
2300                2305                2310

Leu Val
2315
```

IL-34 RECEPTOR ASSAYS AND USES THEREOF

CROSS-REFERENCE TO RELATED APPLICATIONS

This application is a U.S. national stage entry under 35 U.S.C. X371 of PCT International Patent Application No. PCT/US2014/038590, filed May 19, 2014, which claims the benefit of U.S. Provisional Application No. 61/826,356, filed May 22, 2013, the contents of each of which are incorporated herein by reference into the subject application.

STATEMENT OF GOVERNMENT SUPPORT

This invention was made with government support under grant numbers CA032551, CA013330 and RR019352 awarded by the National Institutes of Health. The government has certain rights in the invention.

FIELD OF THE INVENTION

The invention relates to assays for activators and inhibitors of actions of interleukin-34 (IL-34) that are independent of the colony stimulating factor-1 (CSF-1) receptor (CSF-1R) and play a role in development, homeostasis and disease.

BACKGROUND OF THE INVENTION

Throughout this application various publications are referred to in parentheses. Full citations for these references may be found at the end of the specification before the claims. The disclosures of these publications are hereby incorporated by reference in their entireties into the subject application to more fully describe the art to which the subject application pertains.

The CSF-1R kinase (1,2) plays a critical role in the regulation of macrophage and osteoclast production and function (3-6) as well as the development and regulation of other cell types (7-11). The existence of an additional CSF-1R ligand was proposed based on the greater severity of phenotype of homozygous null CSF-1R mice, compared to the phenotype of homozygous CSF-1-null mutant mice (12). A second ligand for the CSF-1R, interleukin-34 (IL-34), with no apparent sequence similarity to any other growth factor, was subsequently identified (13). While IL-34 and CSF-1 compete for binding to the CSF-1R and have similar CSF-1R-mediated effects, they exhibit significant tissue specific and developmental differences in their expression patterns (14). In addition, whereas CSF-1-deficient mice exhibit partial loss of microglia, CSF-1R-deficient mice have no microglia (15). This observation, together with the high expression of IL-34 in brain suggested an important role of IL-34 in microglial development. In agreement with this, IL-34-deficient (IL-34−/−) mice were shown to exhibit severe deficits in microglia (16,76). Despite the similarity of IL-34 and CSF-1 in their CSF-1R-mediated effects (14,17), IL34 mRNA is expressed at a significantly higher level than either Csf1 or Csf1r mRNA in several regions of the early postnatal and adult brain (14) and IL-34 protein is often expressed in regions where there is minimal expression of the CSF-1R or CSF-1-reporter proteins and IL-34 is significantly more active in suppressing neural progenitor cell proliferation and neuronal differentiation than CSF-1 (9).

Protein tyrosine phosphatase receptor type zeta (PTP-ζ) (18,19), a cell-surface receptor and a chondroitin sulfate (CS) proteoglycan (CSPG), is highly abundant in the brain (20), primarily expressed on neural progenitors and glial cells (21-23) and binds to and signals through the action of multiple ligands (24) including the growth factor, pleiotrophin (PTN) (25,26), the cell-surface protein, contactin (CNTN) (27) and the extracellular matrix (ECM) protein, tenascin-R (TN-R) (28). The binding of some of these ligands involves the CS glycosaminoglycan (GAG)-moiety of PTP-ζ (25,29). Ligand binding to PTP-ζ leads to increased tyrosine phosphorylation of down-stream targets, including β-catenin, β-adducin, Src-family kinases (SFK), focal adhesion kinase (FAK), paxillin and extracellular signal-regulated kinase-1/2 (Erk-1/2) (30-37). PTP-ζ is up-regulated in many human cancers, including glioblastomas, and regulates their proliferation and migration (38-40).

The present invention addresses the need for activators and inhibitors of actions of IL-34 that are independent of the CSF-1R receptor and play a role in development, homeostasis and disease.

SUMMARY OF THE INVENTION

The invention provides methods for determining whether or not an agent is a candidate agent for inhibiting interaction between interleukin-34 (IL-34) and protein tyrosine phosphatase receptor type zeta (PTP-ζ) comprising: contacting cells that express PTP-ζ on their surface and that do not express colony stimulating factor-1 receptor (CSF-1R) with IL-34 in the presence of the agent and in the absence of the agent, and measuring a cellular response induced by IL-34, wherein an agent that reduces a cellular response induced by IL-34 is a candidate agent for inhibiting interaction between IL-34 and PTP-ζ, and wherein an agent that does not reduce a cellular response induced by IL-34 is not a candidate agent for inhibiting interaction between IL-34 and PTP-ζ.

BRIEF DESCRIPTION OF THE DRAWINGS

FIG. 7A-7B. LC-MS/MS peptide hits for TN-R and PTP-ζ. (A) TN-R protein sequence from mouse (SEQ ID NO:10). (B) PTP-β/ζ protein sequence from mouse (SEQ ID NO:11). The carbonic anhydrase homology domain (CA), the fibronectin type III repeat (F) and the two phosphatase domains (PTP1 and PTP2), are boxed. The consensus glycosaminoglycan (GAG)-addition sites are underlined and the transmembrane domain is italicized. The several N-linked glycosylation sites are not indicated. The peptide stretch missing in the short isoform is bolded.

DETAILED DESCRIPTION OF THE INVENTION

Figures 1A, 1B, 1C:
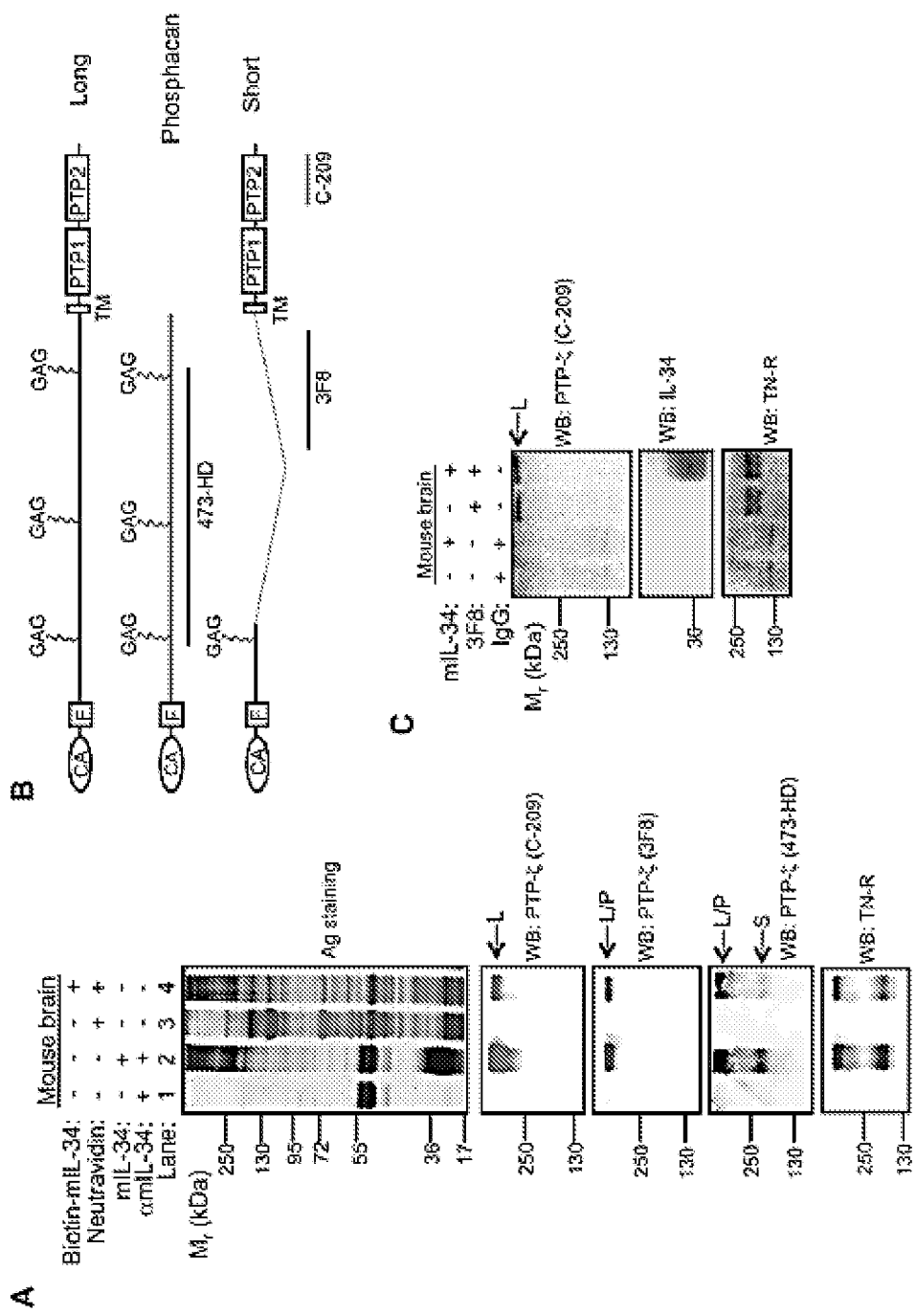
FIG. 1A-1C. Interaction of IL-34 with PTP-ζ in solubilized membrane fractions of mouse brain. (A) N-octyl-β-D-glucoside (OG)-solubilized membrane fractions of mouse brain were incubated (4° C., 16 h) with either immobilized polyclonal rabbit anti-mIL-34 antibody beads that had been preincubated with mIL-34 (lanes 1 & 2), or with biotinylated mIL-34 (lanes 3, 4). The SDS eluates of the IL-34 immunoprecipitates or biotinylated IL-34 complexes (recovered with neutravidin beads) were analyzed by SDS-PAGE with silver staining. The IL-34-associated proteins identified with 99% certainty by mass spectrometry were PTP-ζ and TN-R (FIG. 7). Western blots (WB) indicate the PTP-ζ (L, long isoform, P, phosphacan/soluble isoform and the ~225-kDa short isoform) and TN-R staining bands. Multimeric (52) (slower migrating bands, ~400 kDa) and alternatively spliced (faster migrating bands, 160/180 kDa) variants of TN-R were co-immunoprecipitated, or pulled down. (B) Scheme depicting various PTP-ζ isoforms. Upper panel, the long isoform (active) containing a carbonic anhydrase domain (CA) and a fibronectin type III repeat (F), a transmembrane domain (TM), protein tyrosine phosphatase domains (PTP1 and PTP2) and three glycosaminoglycan (GAG) addition sites. Middle, phosphacan or the secreted isoform lacking the (TM) and PTP domains. Lower, the short isoform (active) missing 860 amino acids of the long isoform. 3F8 and C-209 antibodies recognize the extracellular and intracellular regions of PTP-ζ, respectively and the 473-HD antibody all three isoforms. 3F8 is directed against rat phosphacan and is not as effective in detecting mouse PTP-ζ. C-209 antibody recognizes the short isoform from the mouse brain membrane lysates infrequently. (C) Co-immunoprecipitation of PTP-ζ with IL-34. The OG-solubilized mouse brain membrane fraction was incubated with mIL-34 (4° C., 16 h), immunoprecipitated with immobilized anti-PTP4 (3F8), or isotype control (mIgG1) antibodies and the immunoprecipitates analyzed by gradient SDS-PAGE and western blotting. L, long isoform; P, phosphacan and S, short isoform.

The invention provides a method for determining whether or not an agent is a candidate agent for inhibiting interaction between interleukin-34 (IL-34) and protein tyrosine phosphatase receptor type zeta (PTP-ζ) comprising:

contacting cells that express PTP-ζ on their surface and that do not express colony stimulating factor-1 receptor (CSF-1R) with IL-34 in the presence of the agent and in the absence of the agent, and measuring a cellular response induced by IL-34, wherein an agent that reduces a cellular response induced by IL-34 is a candidate agent for inhibiting interaction between IL-34 and PTP-ζ, and wherein an agent that does not reduce a cellular response induced by IL-34 is not a candidate agent for inhibiting interaction between IL-34 and PTP-ζ.

The terms PTP-ζ and PTP-β/ζ are used interchangeably in this application.

The cells can be, for example, glioblastoma cells, such as, e.g., U251 human glioblastoma cells.

The cells can have been transfected with nucleic acid encoding human PTP-ζ. Human PTP-ζ has the amino acid sequence (ACCESSION P23471, VERSION P23471.4 GI:229485537, SEQ ID NO:12):

```
   1 mrilkrflac iqllcvcrld wangyyrqqr klveeigwsy tgalnqknwg kkyptcnspk
  61 qspinidedl tqvnvnlkkl kfqgwdktsl entfihntgk tveinltndy rvsggvsemv
 121 fkaskitfhw gkcnmssdgs ehslegqkfp lemqiycfda drfssfeeav kgkgklrals
 181 ilfevgteen ldfkaiidgv esvsrfgkqa aldpfillnl lpnstdkyyi yngsltsppc
 241 tdtvdwivfk dtvsisesql avfcevltmq qsgyvmldmy lqnnfreqqy kfsrqvfssy
 301 tgkeeiheav cssepenvqa dpenytsllv twerprvvyd tmiekfavly qqldgedqtk
 361 hefltdgyqd lgailnnllp nmsyvlqiva ictnglygky sdqlivdmpt dnpeldlfpe
 421 ligteeiike eeegkdieeg aivnpgrdsa tnqirkkepq isttthynri gtkyneaktn
 481 rsptrgsefs gkgdvpntsl nstsqpvtkl atekdislts qtvtelppht vegtsaslnd
 541 gsktvlrsph mnlsgtaesl ntvsiteyee eslltsfkld tgaedssgss patsaipfis
 601 enisqgyifs senpetityd vlipesarna sedstssgse eslkdpsmeg nvwfpsstdi
 661 taqpdvgsgr esflqtnyte irvdesektt ksfsagpvms qgpsvtdlem phystfayfp
 721 tevtphaftp ssrqqdlvst vnvvysqttq pvyngetplq psyssevfpl vtpllldnqi
 781 lnttpaassss dsalhatpvf psvdvsfesi lssydgapll pfssasfsse lfrhlhtvsq
 841 ilpqvtsate sdkvplhasl pvaggdllle pslaqysdvl stthaasetl efgsesgvly
 901 ktlmfsqvep pssdammhar ssgpepsyal sdnegsqhif tvsyssaipv hdsvgvtyqg
 961 slfsgpship ipkssliptpt asllqpthal sgdgewsgas sdsefllpdt dgltalniss
1021 pvsvaeftyt tsvfgddnka lskseiiygn etelqipsfn emvypsestv mpnmydnvnk
1081 lnaslqetsv sisstkgmfp gslahtttkv fdheisqvpe nnfsvqptht vsqasgdtsl
1141 kpvlsansep assdpassem lspstqllfy etsasfstev llqpsfqasd vdtllktvlp
1201 avpsdpilve tpkvdkisst mlhlivsnsa ssenmlhsts vpvfdvspts hmhsaslqgl
1261 tisyasekye pvllksessh qvvpslysnd elfqtanlei nqahppkgrh vfatpvlsid
1321 eplntlinkl ihsdeiltst kssvtgkvfa giptvasdtf vstdhsvpig nghvaitavs
1381 phrdgsvtst kllfpskats elshsaksda glvgggedgd tdddgddddd drgsdglsih
1441 kcmscssyre sqekvmndsd thenslmdqn npisyslsen seednrvtsv ssdsqtgmdr
1501 spgkspsang lsqkhndgke endiqtgsal lplspeskaw avltsdeesg sgqgtsdsln
1561 enetstdfsf adtnekdadg ilaagdseit pgfpqsptss vtsensevfh vseaeasnss
1621 hesriglaeg lesekkavip lvivsaltfi clvvlvgili ywrkcfqtah fyledstspr
1681 vistpptpif pisddvgaip ikhfpkhvad lhassgftee fetlkefyqe vqsctvdlgi
1741 tadssnhpdn khknryiniv aydhsrvkla qlaekdgklt dyinanyvdg ynrpkayiaa
1801 qgplkstaed fwrmiwehnv evivmitnlv ekgrrkcdqy wpadgseeyg nflvtqksvq
1861 vlayytvrnf tlrntkikkg sqkgrpsgrv vtqyhytqwp dmgvpeyslp vltfvrkaay
1921 akrhavgpvv vhcsagvgrt gtyivldsml qqiqhegtvn ifgflkhirs qrnylvqtee
1981 qyvfihdtlv eailsketev ldshihayvn allipgpagk tklekqfqll sqsniqqsdy
```

```
2041 saalkqcnre knrtssiipv ersrvgissl sgegtdyina syimgyyqsn efiitqhpll 2101 htikdfwrmi wdhnaqlvvm ipdgqnmaed efvywpnkde pincesfkvt lmaeehkcls 2161 neekliiqdf ileatqddyv levrhfqcpk wpnpdspisk tfelisvike eaanrdgpmi 2221 vhdehggvta gtfcalttlm hqlekensvd vyqvakminl mrpgvfadie qyqflykvil 2281 slvstrqeen pstsldsnga alpdgniaes leslv
```

Cellular response induced by IL-34 can include any of the following. IL-34 can inhibit, for example, one or more of cell proliferation, clonogenicity and/or motility. IL-34 can induce tyrosine phosphorylation of a protein, such as, for example, focal adhesion kinase (FAK) and/or paxillin. IL-34 can also, for example, stimulate differentiation of neural progenitor cells.

The agent can be, for example, an antibody, a monoclonal antibody, a polyclonal antibody, an antibody fragment, a F(ab')$_2$ fragment, a Fab' fragment, a peptide, a peptide nucleic acid, or small chemical compound (e.g., have a molecular weight of 5,000 daltons or less).

The agent can bind to a chondroitin sulfate glycosaminoglycan (GAG) moiety on PTP-ζ or to a GAG mimic.

The agent can be useful, for example, for treatment of a disease or disorder or a defect in neural or microglial development or a defect in homeostasis. The disease or disorder can be, for example, cancer, inflammation, a central nervous system disease, brain injury, neuro-degeneration, a memory deficit, glioblastoma, multiple sclerosis, schizophrenia, or autoimmune disease.

This invention will be better understood from the Experimental Details that follow. However, one skilled in the art will readily appreciate that the specific methods and results discussed are merely illustrative of the invention as described more fully in the claims that follow thereafter.

EXPERIMENTAL DETAILS

Introduction

An unbiased proteomic approach identified PTP-ζ as an IL-34-interacting membrane protein in mouse brain. Using shRNA-mediated suppression of PTP-ζ expression in a CSF-1R-less U251 human glioblastoma cell line, IL-34 was demonstrated to bind specifically to cell-surface PTP-ζ to initiate downstream signaling that leads to the inhibition of cell proliferation, clonogenicity and motility. IL-34-binding to PTP-ζ is dependent on the presence of the CS GAG moiety on PTP-ζ. The demonstration of the existence of a novel IL-34 receptor increases the scope of biological effects of IL-34 in development, homeostasis and disease.

Materials and Methods

Reagents—

Purified mouse IL-34 (mIL-34), human IL-34 (hIL-34) and purified polyclonal rabbit anti-mIL-34 antibodies were from FivePrime Therapeutics, Inc., CA, USA) and human PTN (hPTN) was from R&D (Minneapolis, Minn.). Growth factors were suspended in phosphate buffered saline (PBS) as vehicle mIL-34 and hIL-34 were biotinylated using a 10 molar excess of EZ-Link Sulfo-NHS-LC-LC-Biotin (Thermo Scientific, MA, USA) (15', 20° C.) following manufacturer's instructions. The rabbit anti-C-terminal CSF-1R peptide antibody (C-15) to the mouse CSF-1R (mCSF-1R) and human CSF-1R (hCSF-1R), used for western blotting and immunoprecipitation, has been previously reported (41). Other antibodies used for western blotting were directed against phosphotyrosine (pY-100) and β-catenin (Cell Signaling), pY118paxillin and pY397FAK (Life Technologies, NY, USA); hCSF1R (2-4A5), β-addu-cin, FAK and TN-R (Santa Cruz Biotechnology Inc., CA, USA); paxillin and PTP-ζ (C-209) (BD Biosciences), PTP-ζ (3F8) (DSHB, the University of Iowa); PTP-ζ (473-HD) (Santa Cruz Biotechnology Inc., CA, USA)(42); EF1α (43). Bovine serum albumin (BSA), was from Gemini (CA, USA), Puromycin dihydrochloride, trypan blue, crystal violet, DAPI, shark cartilage CS salts, Proteus vulgaris chondoitinase ABC (chABC) and phalloidin were from SIGMA (MO, USA). Polybrene was from Santa Cruz Biotechnology, Inc. (CA, USA). Neutravidin-Ultralink beads were from Thermo Scientific (MA, USA). Streptavidin-conjugated APC-Cy7 was from Biolegend (CA, USA). LIVE/DEAD® Fixable dead cell stain kits were from Molecular Probes (NY, USA). HTS FluoroBlok™ inserts and 24-well and 6-well tissue culture dishes were from BD Biosciences, Franklin Lakes, N.J. Accutase was from Stem Cell Technologies (Vancouver, BC, Canada). Human PTP-ζ and CSF-1R extracellular domains (ECD) fused immunoglobulin Fc domains (hPTP-ζ-ECD-Fc and hCSF-1R-ECD-Fc) were prepared as described previously for the hCSF-1R-ECD-Fc (13). Human recombinant CSF-1 (hCSF-1) was a gift from Chiron Corp. (Emeryville, Calif., USA). EDC/NHS, HBSP and HBSP+ buffers were from GE Healthcare Biosciences, Pittsburgh, Pa., USA.

Sample Preparation for LC-MS/MS-Identification of the Receptor—

Sub-cellular fractionation was carried out to isolate the membrane fraction from a pool of 2 postnatal day 7 and 2 postnatal day 60 mouse brains. Briefly, mouse brain tissue was homogenized in homogenization buffer (65 mM Tris, 150 mM sodium chloride, 1 mM EDTA, 10 µg/ml aprotinin, 10 µg/ml leupeptin and 1 mM benzamidine, pH 7.4) and the homogenate centrifuged (1000×g, 3 min, 4° C.). The supernatant was further centrifuged (100,000×g, 30 min, 4° C.) and the pellet dissolved in 2% N-octyl-β-D-glucoside (OG), prior to centrifugation (100,000×g, 30 min, 4° C.). The supernatant, containing 26 mg of the OG-solubilized membrane lysate was first pre-cleared by incubation with 60 µg of anti-CSF-1R peptide antibody (C-15) (4° C., 16 h) and then incubated with 24 µg of mIL-34 non-covalently bound to 40 µg of immobilized polyclonal rabbit anti-mIL-34 antibody (4° C., 16 h) mIL-34-anti-mIL-34 antibody complex was serially washed using 0.1 M glycine-HCl, pH 2.2 and 8 M urea and subsequently eluted with 1% SDS. The glycine-HCl and urea washes did not result in dissociation of proteins from mIL-34-anti-mIL-34 antibody complex, as determined by SDS-PAGE and LC-MS/MS. The denatured, reduced and alkylated SDS eluate was further concentrated by ultracentrifugation using 100 kDa cut-off filters and subjected to SDS removal, concentration, trypsinization and detergent extraction with ethyl acetate, as described elsewhere (44,45) followed by LC-MS/MS.

Nanoelectrospray LC-MS/MS Analyses and Protein Identification—

Tryptic digests were loaded and separated using the UltiMate, FAMOS, Switchos nano-HPLC system (LC Packings, Dionex; Sunnyvale, Calif.), connected on-line to a LTQ Linear Ion Trap mass spectrometer (Thermo Fisher Scientific, Waltham, Mass.) and equipped with a nanospray source. The mobile phases consisted of 5% acetonitrile/water, 0.1% formic acid (A) and 80% acetonitrile/water, 0.1% formic acid (B). After injection (15 µl of sample) and loading onto a C18 trap column, 0.3 mm I.D.×5 mm, the tryptic peptides were separated on a C18 analytical HPLC column (75 µm I.D.×15 cm; Pepmap, 3 µm, 100 Å; LC Packings, Dionex; Sunnyvale, Calif.). The flow rate for loading and desalting was 15 µl/min for 30 minutes while the analytical separation was performed at 250 ηl/min. The gradient used was: 2% to 55% B in 65 min; held at 55% B for 10 minutes; increase to 95% B in 5 min and then held at 95% B for 5 minutes. The HPLC eluent was electrosprayed into the LTQ using the nanospray source. After an initial MS-survey scan, m/z 300-1800, MS/MS scans were obtained from three most intense ions using a normalized collision-energy of 35%. DTA files were generated from the raw data files, merged and searched against all species of the NCBInr database (Jul. 2, 2010) using Mascot (version 2.3). The search parameters were: fixed modification—carboxymethyl Cys; variable modifications—N/Q deamidation, oxidized Met, pyro-glu from Q and pyro-glu from E; 2 missed cleavages; peptide mass tolerance of +/−3.5 Da and +/−0.6 Da for the product ions. Scaffold (version 3, Proteome Software Inc., Portland, Oreg.) was used to validate MS/MS based peptide and protein identifications. Peptide identifications were accepted if they could be established at greater than 95% probability and protein identifications were accepted at greater than 99% probability and with unique significant peptide hits ($p<0.05$). Utilizing these criteria 9 proteins were identified excluding trypsin and keratin (6 of them were membrane proteins). The two proteins identified with the highest protein score were TN-R and PTP-ζ. The Mascot protein score for TN-R (3 matching protein accession numbers: gi|148707401, gi|226958549 or gi|61216646; 139 kDa) was 932 with protein sequence coverage of 15% protein. The protein score for PTP-ζ (gi|124486807) was 555 with 5% coverage.

Cell Lines, Cell Culture Conditions and Cell Treatments—

The U251, SNB19 and U87MG human glioblastoma cell lines were a gift of Dr. J. Segall, Albert Einstein College of Medicine, NY, USA). NIH-3T3-hCSF-1R cells (46) were a gift from Dr. Martine Roussel, St. Jude Children's Research Hospital, Memphis, Tenn. Mouse BAC1.2F5 macrophages (47) were cultured in 36 ng/ml hCSF-1 as described (48). U251 cells were cultured in DMEM-high glucose (GIBCO, Grand Island, N.Y., USA) supplemented with 10% FCS and passaged when confluent. Prior to stimulation with hIL-34 or hPTN, cells were depleted of growth factors by incubation in DMEM-high glucose supplemented with 0.2% BSA for 16 h, except where otherwise indicated. Following stimulation, cells were washed in ice-cold PBS and recovered by scraping and centrifugation, except where otherwise indicated. For chABC-treatment, serum-starved U251 cells were incubated with 4.2 U/ml chABC (37° C., 1 h 30') and washed extensively, before processing for flow cytometry as described below. For treating membrane lysates, 0.3 U/ml chABC was used.

Generation of U251 PTP-ζ Knock-Down (KD) Cells—

Lentiviral particles ($5×10^4$ IFU) carrying a pool of three different PTP-ζ shRNA or scrambled shRNA plasmids (Santa Cruz Biotechnology, CA, USA) were used to infect $3×10^4$ U251 cells (50% confluent) in the presence of 5 µg/ml polybrene in 6-well dishes (37° C., 16 h). Vector-containing cells were selected using 5 µg/ml of puromycin dihydrochloride and the resistant colonies were further sub-cloned by serial dilution method in 96-well plates. The efficiency of knock-down was estimated by western blotting whole cell lysates from the puromycin resistant clones.

Immunoprecipitation and Western Blot Analysis—

Membrane fractions of mouse brain and of BAC1.2F5 macrophages, NIH-3T3-hCSF-1R cells or U251 cells were solubilized in homogenization buffer (65 mM Tris, 150 mM sodium chloride, 1 mM EDTA, 10 µg/ml aprotinin, 10 µg/ml leupeptin and 1 mM benzamidine, pH 7.4) containing the appropriate concentration of OG (brain membrane 2%; cell membrane 1%) and incubated (4° C., 16 h) with either immobilized purified polyclonal rabbit anti-mIL-34 antibody beads (preincubated with mIL-34), biotinylated mIL-34, biotinylated hIL-34 (a gift from FivePrime Therapeutics, Inc., CA, USA), or anti-hCSF-1R antibodies. The biotinylated IL-34 complexes were recovered by incubation with neutravidin-agarose and SDS eluates of IL-34 pull-down and immunoprecipitates analyzed by SDS-PAGE and western blotting (WB). For co-immunoprecipitation experiments, mouse brain membrane lysates were pre-incubated with mIL-34 (4° C., 16 h), prior to incubation with anti-PTP-ζ (3F8) antibodies. For stimulation and/or immunoprecipitation experiments, serum-starved U251 cells were incubated with hPTN or hIL-34 (120 ng/ml) at 37° C. and NP-40 cell lysates (using 1% NP-40, 10 mM Tris HCl, 50 mM NaCl, 30 mM $Na_4P_2O_7$, 50 mM NaF, 100 µM Na3VO4, 5 µM $ZnCl_2$, 1 mM benzamidine, 10 µg/ml leupeptin, and 10 µg/ml aprotinin, pH 7.2) were subjected to immunoprecipitation using antibodies to FAK and paxillin.

Flow Cytometry—

For cell-surface IL-34 binding, serum-starved U251 cells were gently harvested with 2 mM EDTA in PBS, pH 7.4, washed and $1×10^6$ cells were pre-incubated with a 10 molar excess of hIL-34 in Hank's Balanced Salt Solution (HBSS) (Life Technologies) in the presence of 1% BSA (4° C., 1 h). After extensive washing, specific IL-34 binding was detected by incubating the cells with 2 µg/ml biotinylated hIL-34 (4° C., 1 h), and, subsequently, with 5 µg/ml streptavidin-conjugated APC-Cy7. Flow cytometry was performed using FACS Canto II (BD Biosciences, NC, USA) (gating on viable cells). The FlowJo software (Treestar, USA) was used for data analysis. For detection of hCSF-1R expression, serum-starved $2×10^5$ U251 cells were incubated with 5 µg/ml rat anti-hCSF-1R monoclonal antibody (2-4A5) or control rat $IgG_1$ (e-Biosciences, CA, USA) (4° C., 45'), then subsequently incubated with 5 µg/ml FITC-conjugated F(ab')2-anti-Rabbit IgG (e-Biosciences, CA, USA) prior to flow cytometric analysis as previously described. For the analysis of FLAG-tagged IL-34 and CSF-1 binding to U251 cells by flow cytometry, the expression, purification and quantitation of the concentrations of IL-34-FLAG and CSF-1-FLAG proteins in the medium of the transfected 293T cells, as well as the detection of cell binding with biotin-labeled anti-FLAG M2 antibody, were carried out as described (17).

Cell Proliferation and Clonogenic Assays—

U251 cells were seeded at 25% confluency in DMEM-high glucose supplemented with 10% FCS in 24-well tissue culture dishes. 24 h later, cells were washed twice with PBS and medium was replaced with DMEM-high Glucose supplemented with 1% FCS and vehicle (PBS) or hIL-34 (20 ng/ml) or hPTN (20 ng/ml). Cell proliferation was assessed by counting viable (Trypan-Blue excluding) cells harvested at the indicated times. For the clonogenic assays, semi-confluent U251 cells were exposed to a 16 h pulse of hPTN (20 ng/ml), hIL-34 (20 ng/ml) or vehicle (PBS). After that, cells where harvested by Accutase digestion, filtered through a 40 µm mesh to ensure single cellularity and subsequently seeded at 1000 cells/well into 6-well dishes in the presence of 25% conditioned medium (from the 16 h pulse). The number of colonies composed of >50 cells was scored by crystal violet staining 8 days later.

Cell Migration Assays—

For wound healing assays, serum-starved (16 h) monolayer cultures of U251 cells were scratched and the wound allowed to heal in the continued absence of serum and in the presence of either hPTN or hIL-34 (200 ng/ml). For haptotactic migration assays, $10^5$ serum-starved U251 cells were assayed (37° C., 4 h) in a 24-well transwell chamber. Inserts were pre-coated with BSA (20 µg/ml, no growth factor) or hPTN (5 µg/ml) or hIL-34 (10 µg/ml) for 2 h at room temperature prior to the assay. For the random migration studies (37° C., 4 h), hPTN or hIL-34 (1 µg/ml) was added to both sides of the transwell chamber. Cells were scraped from the upper side of the chamber and the lower side was stained with DAPI and phalloidin. Phalloidin-stained cells were counted using a fluorescence microscope.

Nanoelectrospray LC-MS/MS Analyses and Protein Identification—

Tryptic digests were loaded and separated using the UltiMate, FAMOS, Switchos nano-HPLC system (LC Packings, Dionex; Sunnyvale, Calif.), connected on-line to a LTQ Linear Ion Trap mass spectrometer (Thermo Fisher Scientific, Waltham, Mass.) and equipped with a nanospray source. The mobile phases consisted of 5% acetonitrile/water, 0.1% formic acid (A) and 80% acetonitrile/water, 0.1% formic acid (B). After injection (15 µL of sample) and loading onto a C18 trap column, 0.3 mm I.D.×5 mm, the tryptic peptides were separated on a C18 analytical HPLC column (75 µm I.D.×15 cm; Pepmap, 3 µm, 100 Å; LC Packings, Dionex; Sunnyvale, Calif.). The flowrate for loading and desalting was 15 µL/min for 30 minutes while the analytical separation was performed at 250 ηL/min. The gradient used was: 2% to 55% B in 65 min; hold at 55% B for 10 minutes; increase to 95% B in 5 min and hold at 95% B for 5 minutes. The HPLC eluent was electrosprayed into the LTQ using the nanospray source. After an initial MS-survey scan, m/z 300-1800, MS/MS scans were obtained from three most intense ions using a normalized collision-energy of 35%. DTA files were generated from the raw data files, merged and searched against all species of the NCBInr database (Jul. 2, 2010) with Mascot (version 2.3). The search parameters used were: fixed modification—carboxymethyl Cys; variable modifications—N/Q deamidation, oxidized Met, pyro-glu from Q and pyro-glu from E; 2 missed cleavages; peptide mass tolerance of +/−3.5 Da and +/−0.6 Da for the product ions. Scaffold (version 3, Proteome Software Inc., Portland, Oreg.) was used to validate MS/MS based peptide and protein identifications. Peptide identifications were accepted if they could be established at greater than 95.0% probability and protein identifications were accepted at greater than 99.0% probability and unique significant peptide hits (p<0.05). With these criteria 9 proteins were identified excluding trypsin and keratin (6 of them were membrane proteins). The 2 proteins identified with the highest protein score were TN-R and PTP-ζ. The Mascot protein score for TN-R (3 matching protein accession numbers: gi|148707401, gi|226958549 or gi|61216646; 139 kDa) is 932 with protein sequence coverage of 15% protein. The protein score for PTP-ζ (gi|124486807) is 555 with 5% coverage.

PTP-ζ shRNA Sequences are as Follows—

```
Hairpin sequence (SEQ ID NO: 1):
5'-GATCCCCAGATTTCTACCACAACATTCAAGAGATGTTGTGGTAGAA
ATCTGGTTTTT-3'

Corresponding siRNA sequences:
Sense:
(SEQ ID NO: 2)
5'-CCAGAUUUCUACCACAACAUU-3'

Antisense:
(SEQ ID NO: 3)
5'-UGUUGUGGUAGAAAUCUGGTT-3'

Hairpin sequence (SEQ ID NO: 4):
5'-GATCCCCACAGAGATGGTTCTGTATTCAAGAGATACAGAACCATCT
CTGTGGTTTTT-3'

Corresponding siRNA sequences:
Sense:
(SEQ ID NO: 5)
5'-CCACAGAGAUGGUUCUGUAtt-3'

Antisense:
(SEQ ID NO: 6)
5'-UACAGAACCAUCUCUGUGGtt-3'

Hairpin sequence (SEQ ID NO: 7):
5'-GATCCCGAAGGAACTGTCAACATATTCAAGAGATATGTTGACAGTT
CCTTCGTTTTT-3'

Corresponding siRNA sequences:
Sense:
(SEQ ID NO: 8)
5'-CGAAGGAACUGUCAACAUAtt-3'

Antisense:
(SEQ ID NO: 9)
5'-UAUGUUGACAGUUCCUUCGtt-3'.
```

Surface Plasmon Resonance (SPR) Binding Analyses—

SPR binding analyses were performed at 25° C. on Biacore instruments. For binding of hIL-34 and hCSF-1 to immobilized hPTP-ζ- and hCSF-1R-ECD-Fcs (Biacore T100), all flow cells of a CM4 sensor chip were activated with EDC/NHS (7 min, 10 µl/min) and recombinant Protein A (Pierce, 21184, 50 µg/ml in 10 mM Na acetate, pH 4.5) was applied (7 min, 10 µl/min) Following immobilization (≥2500 RU of Protein A per flow cell), all flow cells were blocked with 1M ethanolamine-HCl, pH 8.5. hPTP-ζ-ECD-Fc (25 µg/ml) and hCSF-1R-ECD-Fc (7 µg/ml) in HBSP were captured (~300 RU and 97 RU respectively) on individual flow cells and binding analyses performed with different concentrations of recombinant hCSF-1 or hIL-34 in HBSP+ or HBSP+ with 3 µg/ml CS (shark cartilage, Sigma, C4384). The protein A surface was regenerated with 10 mM Glycine-HCl, pH 1.5. For binding of hIL-34 to brevican, different concentrations of hIL-34 in HBSP+ were passed over brevican immobilized on the chip. Binding of hTN-R to IL-34 and to hPTP-ζ ECD-Fc (Biacore 3000) was carried out at 25° C. by immobilizing IL-34 (pH 7.0) and hPTP-ζ ECD-Fc (pH 4.05) directly onto flow cells of a CM5 sensor chip (≥2800 RU per flow cell) and passing over different concentrations of hTN-R. Kds were calculated according to the steady state model using BIAevaluation Software (GE Lifesciences). All sensorgrams were double-referenced.

Immunofluorescence Microscopy—

Anesthetized mice were transcardially perfused with ice-cold 0.25 mg/ml heparin in PBS (10 ml) followed by 4% paraformaldehyde (50 ml), their brains harvested, post-fixed overnight in 4% PFA, equilibrated in 20% sucrose, flash frozen in a cryomatrix resin and stored at −80° C. prior to use. For immunofluorescence microscopy, specimens were cryosectioned (30 µm sections), immunostained with a mature neuronal marker (NeuN, mIgG1, 1:100, Millipore); an adult neural stem cell marker (GFAP, mouse IgG2b, 1:300, Millipore); IL-34 (polyclonal rabbit IgG, 1:500, Five Prime Therapeutics, CA, USA); PTP-ζ (3F8, mouse IgG1, 1:1250, Developmental Studies Hybridoma Bank, IA); TN-R (polyclonal rabbit IgG, 1:50, Santa Cruz Biotechnology, CA); photographed either with an Olympus BX51 microscope (Tokyo Japan) coupled with a Sensicam digital camera (Cooke Corporation, Michigan, USA), or with a Zeiss Duo V2 Laser Confocal Microscope. Images were subsequently processed with Image J and Photoshop CS5 software programs.

Statistics—

Student's t test was used to assess the statistical significance of the data sets.

Results

Mouse IL-34 (mIL-34) Associates with Mouse Brain PTP-ζ and TN-R—

Figures 7A, 7B:
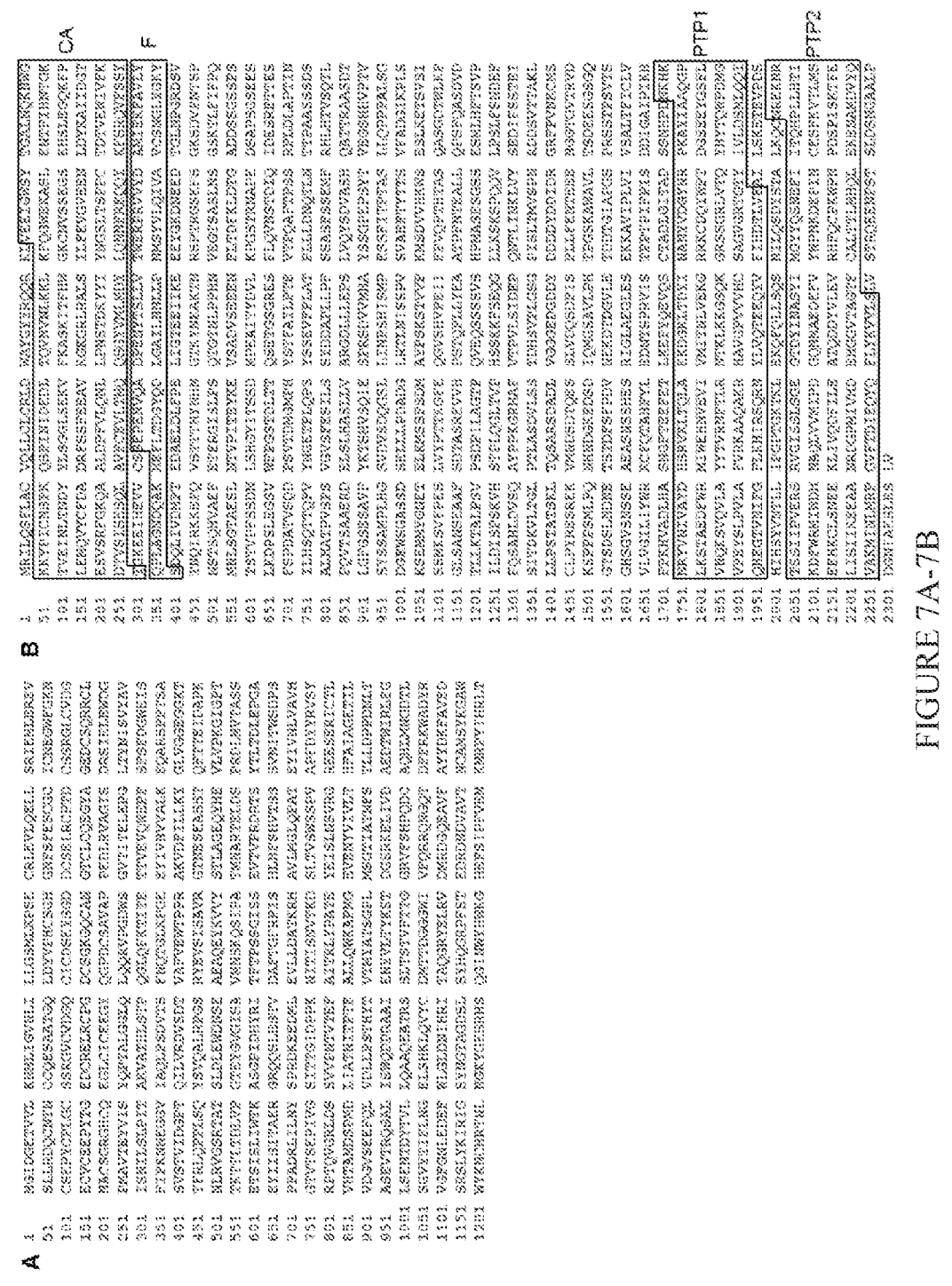

Compared with the expression patterns of CSF-1 and the CSF-1R, IL-34 expression in postnatal mouse brain, is spatially, temporally and quantitatively distinct (9,14). This prompted a search for additional IL-34 receptor(s) in detergent-solubilized postnatal mouse brain membranes. To identify novel IL-34-interacting proteins, mouse brain membrane lysate, depleted of the known IL-34 receptor, CSF-1R, was subjected to affinity chromatography with mIL-34 non-covalently bound to an immobilized polyclonal rabbit anti-mIL-34 antibody. Bound proteins were eluted with SDS and processed for mass spectrometry (MS). The two eluted proteins identified with highest certainty were PTP-ζ, a cell-surface RPTP and its ECM ligand, TN-R (FIG. 7). SDS-PAGE and silver staining of the SDS eluates of the mIL-34-anti-mIL-34 antibody affinity purification, or of IL-34-associated proteins prepared by the alternative approach of binding to biotinylated-mIL-34 and capturing the complexes with immobilized neutravidin demonstrated a diffuse band of ~400 kDa, another broad band at ~225 kDa, as well as 160/180 kDa species (FIG. 1A, lanes 1-4, upper panel).

Due to alternative splicing, PTP-ζ exists in three isoforms, one soluble and two membrane-spanning molecules (FIG. 1B). The ~400-kDa band was confirmed by western blotting to cover stainable bands corresponding to both the long (49) and phosphacan isoforms of PTP-ζ (50,51) as well as multimeric TN-R (52). The ~225-kDa band co-migrated with a band that stained with the 473-HD antibody (42), that sensitively stains the short PTP-ζ isoform and which also stained in the region of the ~400 kDa band corresponding to the long receptor and the phosphacan isoforms. The 160/180-kDa proteins, with the apparent $M_r$ of the monomeric TN-R isoforms (52), co-migrated with the faster bands western blotted with the anti-TN-R antibody (FIG. 1A, lanes 1-4, lower panels), corresponding to the monomeric TN-R isoforms. To confirm the PTP-ζ binding results, mouse brain membrane lysate was incubated with mIL-34 and a reciprocal co-immunoprecipitation experiment was performed, immunoprecipitating with 3F8, an antibody that recognizes both the soluble and the long membrane-spanning isoforms of rat PTP-ζ (53) (FIG. 1B) and western blotting with anti-IL-34 and anti-TN-R antibodies (FIG. 1C). These results show that mIL-34 forms a complex with the larger membrane-spanning isoform of PTP-ζ and with TN-R. However, consistent with earlier reports that the TN-R binding to PTP-ζ is ligand-independent (28,54), TN-R binding to PTP-ζ was IL-34-independent (FIG. 1C).

SPR analysis of hIL-34 binding to the full-length hPTP-ζ ECD-Fc (Kd~10-7M) and the hCSF-1R-ECD-Fc (Kd~10-12M) revealed dose-dependent binding to both, whereas hCSF-1 only bound to the hCSF-1R-ECD-Fc (Kd~10-11M). Similar analyses of the binding of IL-34 to two other proteoglycans identified by MS, hTN-R (Kd~10-6M) and human brevican (Kd=3×10-6M), revealed lower affinity binding, whereas the interaction of TN-R with the hPTP-ζ ECD-Fc was of higher affinity (Kd~10-8M), but lower than previously reported (28,54).

Human IL-34 (hIL-34) Binds to Cell-Surface PTP-ζ on U251 Glioblastoma Cells—

Figures 2A, 2B, 2C:
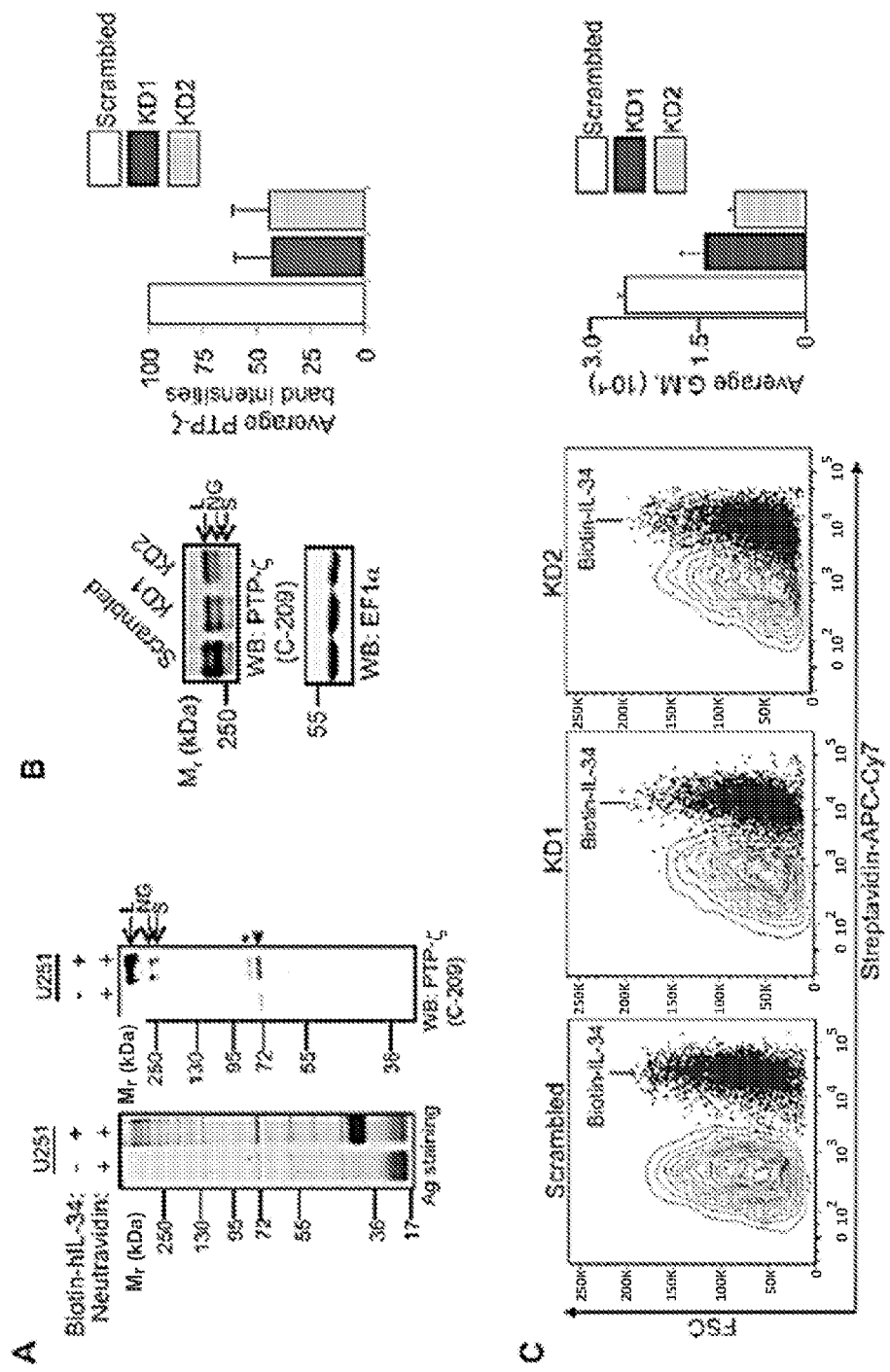
FIG. 2A-2C. IL-34 binds cell-surface PTP-ζ in U251 human glioblastoma cells. (A) Interaction of IL-34 with PTP-ζ in OG-solubilized U251 cell membrane fractions. Membranes lysates were incubated with biotinylated hIL-34 (4° C., 16 h), the complexes captured with neutravidin beads (4° C., 6 h), eluted with SDS and analyzed by SDS-PAGE and silver staining, or by western blotting (WB) with antibodies to PTP-ζ. Arrowhead, non-specific band; asterisk, PTP-ζ proteolytic product (51); L, long isoform; NG, non-glycosaminoglycan form; S, short isoform. (B) Reduced PTP-ζ expression in PTP-ζ KD U251 clones. Left panel; PTP-ζ and control (EF1α) western blots of OG-solubilized whole cell lysate from cells expressing scrambled, or PTP-ζ (KD1 and KD2) shRNAs. Right panel, quantitation of the combined intensities of the three bands (L, NG, S) from two independent experiments (average±range). (C) Flow cytometric analysis of hIL-34 binding to PTP-ζ KD U251 lines. Serum-starved control (scrambled) and KD (1 & 2) cells were either untreated, incubated with 5 μg/ml biotinylated hIL-34, then subsequently incubated with streptavidin-conjugated APC-Cy7 prior to flow cytometric analysis, gating on viable cells. G.M., geometric means of signal intensities of duplicate experiments (average±range).
Figures 8A, 8B, 8C:
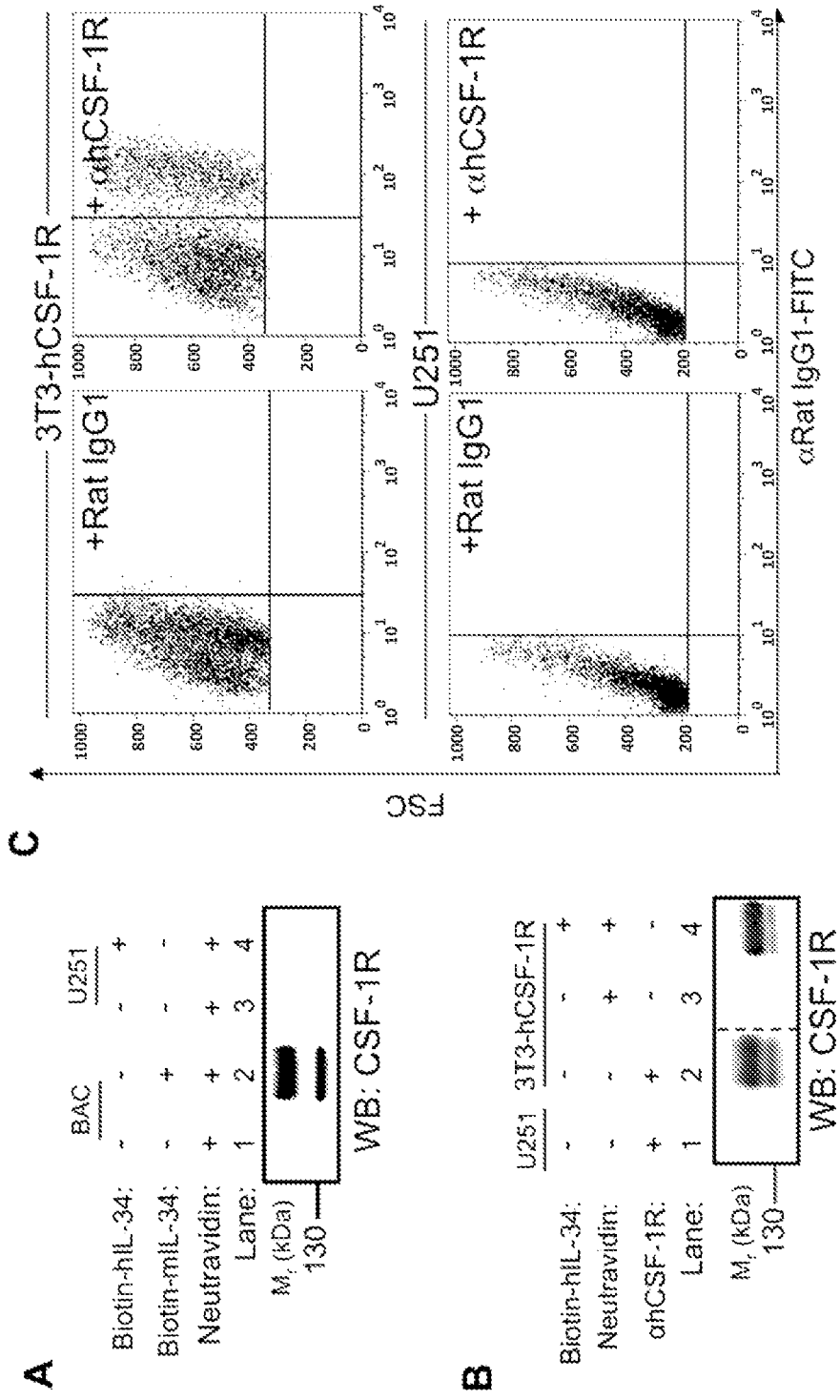
FIG. 8A-8C. U251 cells lack the CSF-1R. (A) Failure of hIL-34 to bind to CSF-1R on U251 cells. N-octyl-β-D-glucoside (OG)-solubilized membrane fractions of BAC1.2F5 (lanes 1 & 2) and U251 (lanes 3 & 4) cells were incubated overnight at 4° C. with biotinylated mIL-34 (lanes 1 & 2) or biotinylated hIL-34 (lanes 3 & 4). The biotinylated IL-34 complexes were recovered by incubation with neutravidin and SDS eluates containing the complexes analyzed by SDS-PAGE and western blotting (WB) with an antibody that equivalently recognizes both mCSF-1R and hCSF-1R. (B) Absence of the CSF-1R in U251 cells. N-octyl-β-D-glucoside (OG)-solubilized membrane fractions of U251 human glioblastoma (lane 1) and NIH-3T3-hCSF-1R (lanes 2-4) cells were incubated overnight at 4° C. with anti-hCSF-1R antibody (lanes 1, 2) or biotinylated hIL-34 (lanes 3, 4). The biotinylated IL-34 complexes were recovered by incubation with neutravidin and SDS eluates of IL-34 pull-down and CSF-1R immunoprecipitates analyzed by SDS-PAGE and western blotting (WB) with antibodies to hCSF-1R. (C) Further verification of the lack of CSF-1R expression on U251 cells. Flow cytometric analyses of $2 \times 10^5$ viable 3T3-hCSF-1R and U251 cells were incubated with 5 μg/ml of rat monoclonal anti-hCSF-1R antibody, or rat IgG1 (isotype control) for 30 min at 4° C., washed with PBS and further incubated with 5 μg/ml of anti-rat IgG1-conjugated FITC for 30 min at 4° C.

Since membrane-spanning PTP-ζ, rather than TN-R, is a known signal-transducing receptor for several ligands (24-28), it was determined whether PTP-ζ also functions as a receptor for IL-34. As PTP-ζ is upregulated in human glioblastomas (38-40), glioblastoma cell lines U251, SNB19 and U87MG were tested for PTP-ζ expression. All the tested cell lines expressed high levels of PTP-ζ. U251 was selected for human IL-34 (hIL-34)-binding studies since it does not express the CSF-1R (FIG. 8). Supporting the observations in mouse brain membrane (FIG. 1A), biotinylated-hIL-34 primarily formed complexes with the long, membrane-spanning, ~400 kDa PTP-ζ (50) and to a lesser extent with the non-glycosaminoglycanylated 300 kDa (55) and the short 220 kDa (49) isoforms (FIG. 2A) in U251 membrane lysates. However, TN-R was not observed in the biotinylated-hIL-34 pull-down fractions of U251 membranes, suggesting that IL-34 probably binds to PTP-ζ in a TN-R-independent manner. Clones stably-expressing PTP-ζ shRNA (KD cells) expressed lower levels of PTP-ζ protein than clones expressing scrambled shRNA (scrambled cells) (FIG. 2B). Scrambled cells expressed higher levels of total soluble PTP-ζ than uninfected cells, indicating that lentiviral infection per se causes cellular PTP-ζ upregulation. Consistent with the dependence of IL-34 binding on PTP-ζ expression, flow cytometric studies demonstrated that the ability of biotinylated hIL-34 to bind to the cell-surface of intact U251 cells was reduced in PTP-ζ KD cells (FIG. 2C), particularly in KD2 cells. Thus these results show that hIL-34 binds to PTP-ζ at the surface of intact U251 cells. The specificity and binding of IL-34 to U251 cells was also investigated in binding experiments with FLAG-tagged human IL-34 and FLAG-tagged human CSF-1 (17). At equivalent concentrations, IL-34-FLAG showed robust binding, whereas CSF-1-FLAG failed to bind and IL-34-FLAG exhibited dose-dependent binding, covering a wide concentration range (0.1 pM-1 nM).

hIL-34 Inhibits U251 Proliferation, Clonogenicity and Motility in a PTP-ζ-Dependent Manner—

Figures 3A, 3B:
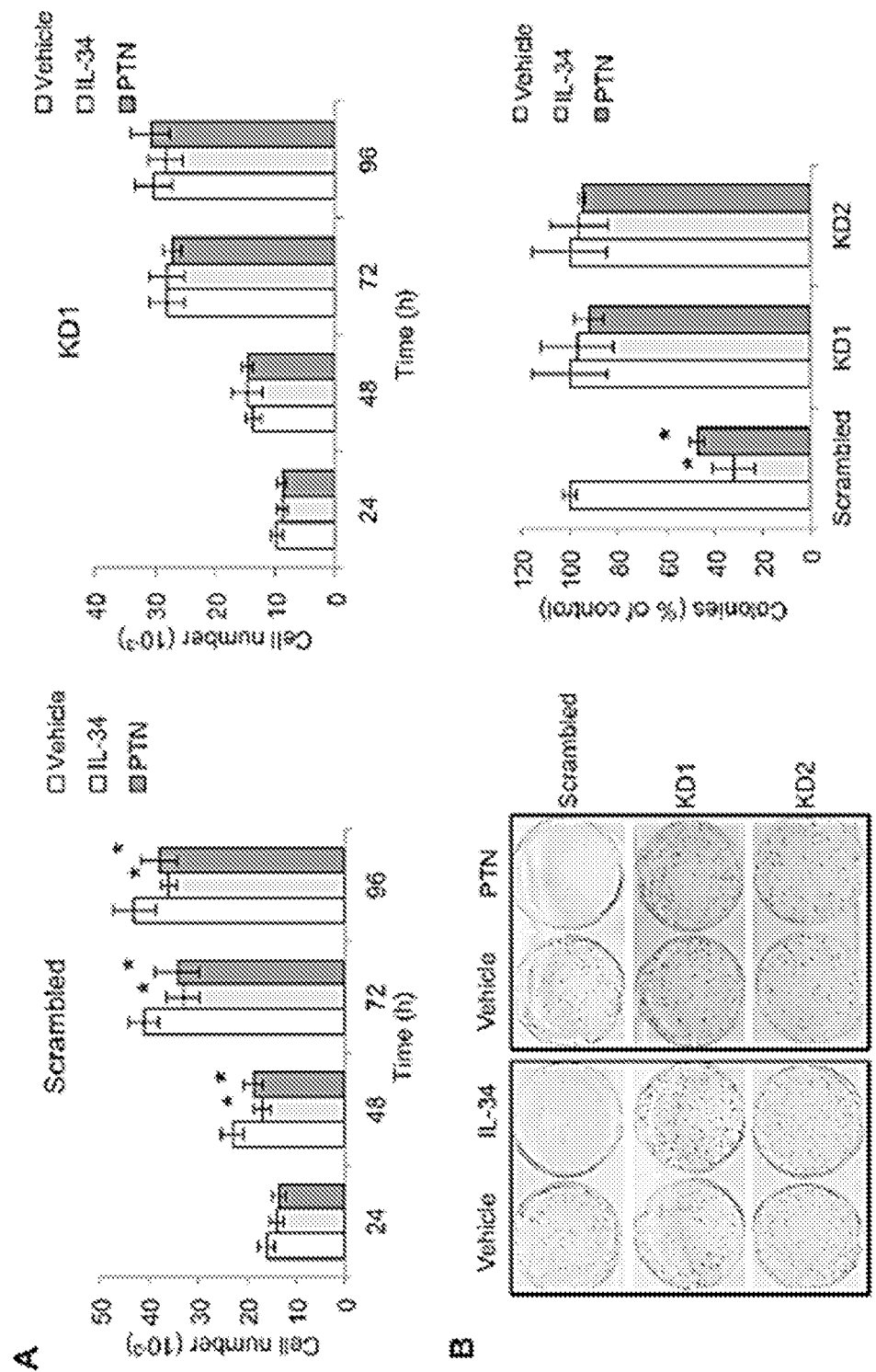
FIG. 3A-3B. IL-34 inhibits growth and clonogenicity of U251 glioblastoma cells in a PTP-ζ-dependent manner (A) Cell proliferation assay. Control (left panel) or PTP-ζ KD (right panel) cells were incubated with the indicated factors for the indicated times and the viable cell numbers assessed by trypan blue exclusion staining (B) Clonogenic assay. Left panel, micrographs of colony forming assays of U251 cells incubated with vehicle or IL-34. Right panel, histograms showing average colony counts from triplicate experiments. (A) and (B), Means±SD; n=3; *, significantly different from cells incubated with vehicle alone, p<0.05.

PTP-ζ-signaling is involved in neuronal migration (56) and neuritogenesis (57) in mouse and in the in vitro and in vivo growth of human glioblastomas (39,58,59). As previous studies have shown that PTN inhibits the growth of glioblastomas, to determine the functional relevance of PTP-ζ receptor engagement by IL-34, the effects of IL-34 and PTN were tested on the U251 glioblastoma cells expressing either PTP-ζ or scrambled (control) shRNAs. Either IL-34 or PTN treatment slightly, but significantly, reduced the growth of scrambled U251 cells over a 96 h time period (~20% reduction in IL-34 vs vehicle-treated control cells, FIG. 3A left panel), while not affecting the growth of the PTP-ζ KD U251 cell lines (FIG. 3A right panel). The effects of IL-34 and PTN on the colony-forming-ability of infected U251 cells were also examined After a 16 h pulse with IL-34 or PTN, cells were seeded at clonal density and the colonies formed at 8 days were stained and counted. IL-34 or PTN treatment strongly decreased the clonogenicity of scrambled U251 cells (reductions of 68% for IL-34 and 53% for PTN, vs vehicle control cells), without significantly affecting the clonogenicity of PTP-ζ KD cells (FIG. 3B, left and right panels).

Figures 4A, 4B, 4C, 4D:
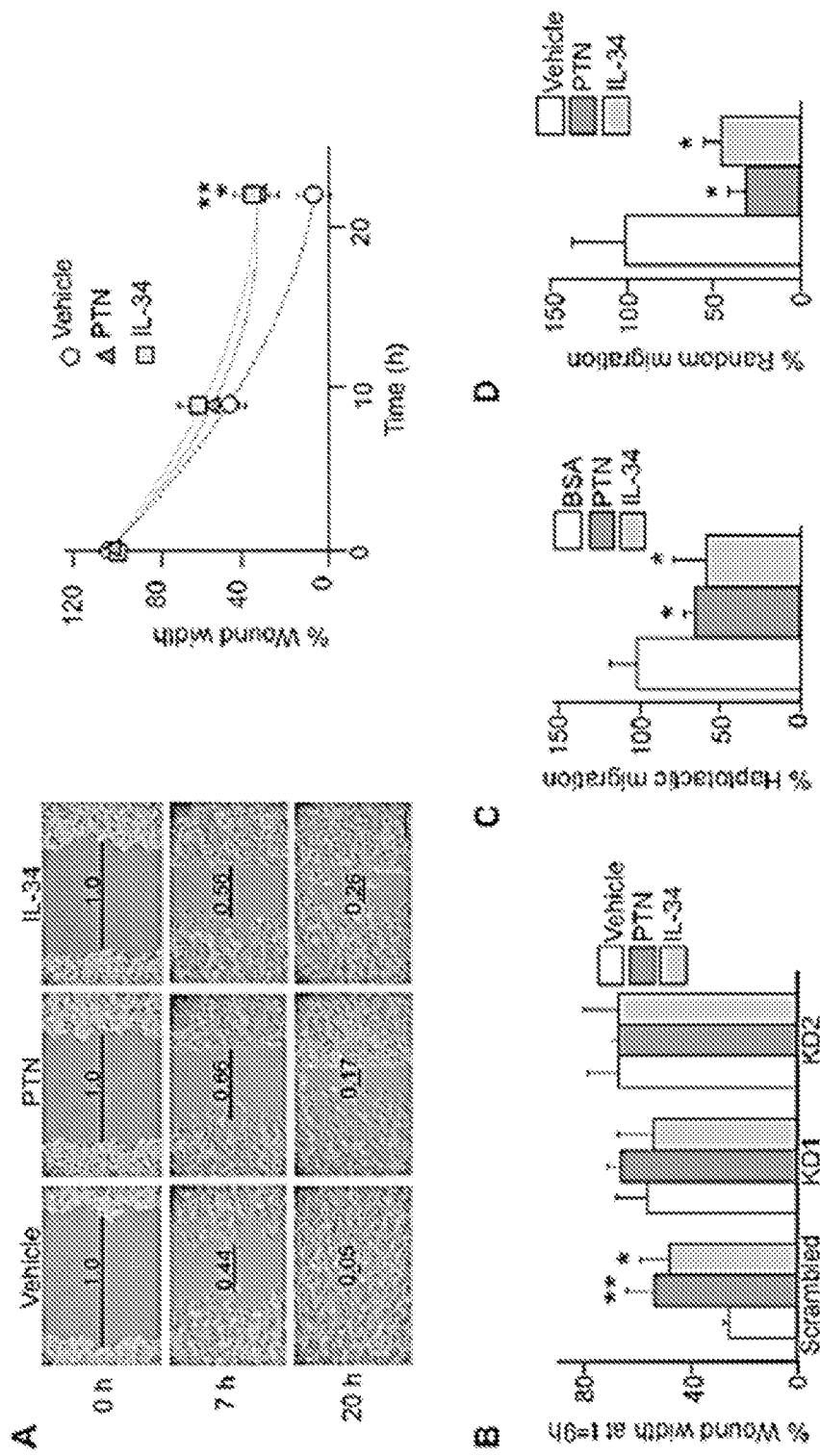
FIG. 4A-4D. IL-34 inhibits PTP-ζ-dependent U251 motility. (A) Inhibition of U251 monolayer wound healing by IL-34. Left panel, numbers above the horizontal lines indicate the fraction of the initial wound width at the time of scratching. Scale bar, 100 μM. Right panel, quantitation (means±SD; n=3). (B) Quantitation of wound healing by control and PTP-ζ KD U251 cells at 9 h, in the presence of PTN or IL-34 (means±SD; n=3). (C) Inhibition of haptotactic migration by IL-34. Migration is expressed as a percent of cells migrated in the BSA control (means±SD; n=3, ≥15 fields per condition). (D) Inhibition of random migration by IL-34. Migration is expressed as a percent of cells migrated in no GF (vehicle) control (means±SD; n=3, ≥10 fields per condition). *, p<0.05 and **, p<0.01.

As PTN was also previously shown to affect glioblastoma cell migration (38-40), to investigate the role of IL-34 in PTP-ζ-mediated glioblastoma cell migration, the effects of IL-34 and PTN were first compared on the wound-healing rates of scrambled and PTP-ζ KD cells (FIG. 4A). In the absence of added ligand(s), KD clones exhibited a slower rate of wound healing, indicating that the constitutively active PTP-ζ receptor facilitates U251 migration (e.g. time taken for 50% wound closure [$t_{50}$] for KD2 cells was >20 h, compared to 5.5 h for scrambled cells). Consistent with ligand-induced inactivation of the receptor (30,32,60), PTN ($t_{50}$=10 h), or IL-34 ($t_{50}$=11.5 h) significantly inhibited wound healing in uninfected cells (vehicle $t_{50}$=7.5 h). Furthermore, neither IL-34, nor PTN could suppress PTP-ζ KD cell wound healing (FIG. 4B), thereby indicating that suppression of healing by either ligand is mediated through PTP-ζ. To determine whether IL-34 and PTN suppress directed migration a haptotaxis assay was used (FIG. 4C), in which PTP-ζ ligands were shown to be more effective in regulating migration than in a conventional chemotaxis assay (61,62). Both IL-34 as well as PTN, when coated on the bottom of the membrane, suppressed migration of U251 cells (FIG. 4C). To determine whether IL-34 and PTN also inhibit random migration, migration of the cells was examined through membranes containing these growth factors on both sides. Both IL-34 as well as PTN inhibited the random migration of the cells (FIG. 4D). Together, these results demonstrate that IL-34 suppresses proliferation, clonogenicity and motility of U251 cells in vitro, in a PTP-ζ-dependent manner.

hIL-34 Enhances PTP-ζ-Mediated Tyrosine Phosphorylation of FAK and Paxillin in U251 Cells—

Figures 5A, 5B, 5C:
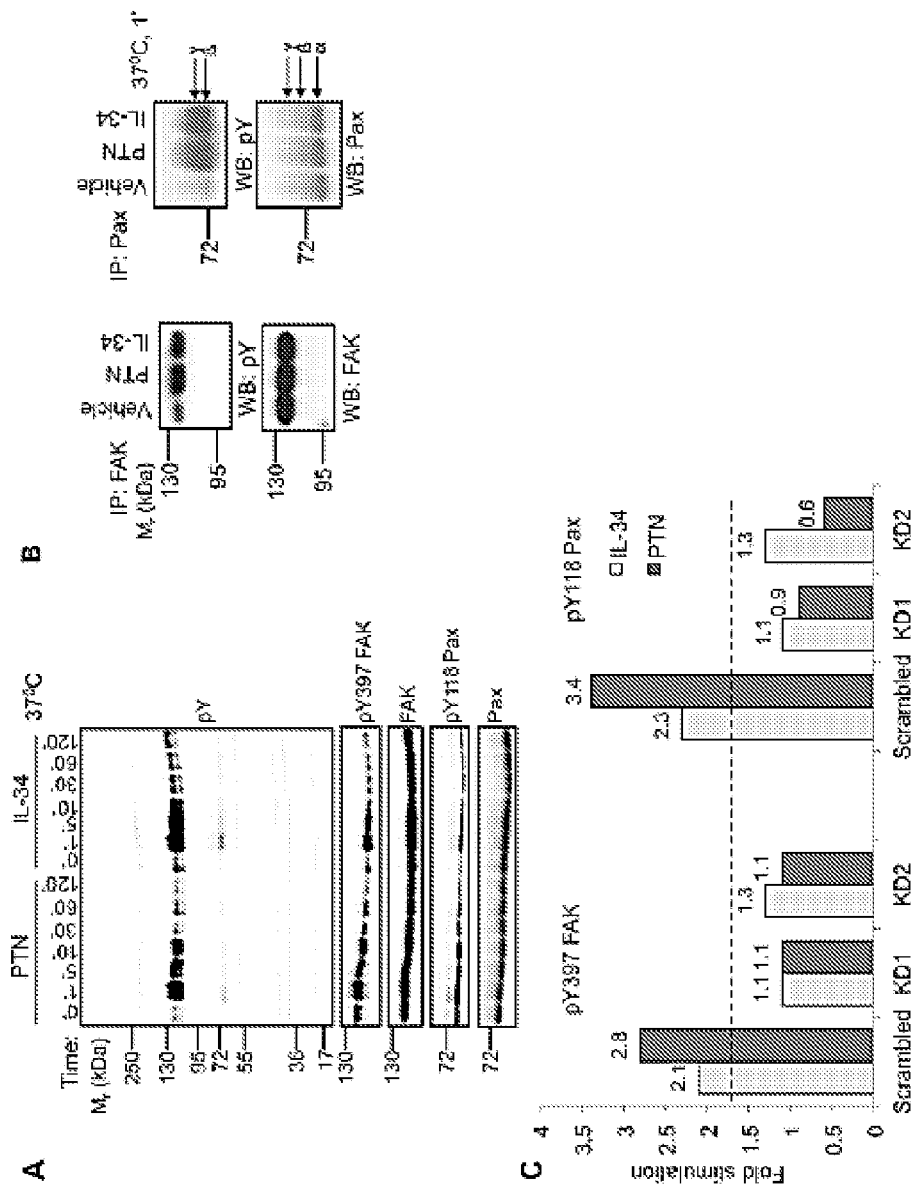
FIG. 5A-5C. IL-34 binding to PTP-ζ enhances tyrosine phosphorylation of FAK and Paxillin, in U251 cells. (A) Kinetics of tyrosine phosphorylation in response to IL-34. SDS-PAGE and western blot analysis of NP-40 lysates from U251 cells treated with IL-34 or PTN harvested at the indicated times and stained as shown. FAK, focal adhesion kinase; Pax, paxillin. (B) Immunoprecipitates of FAK (left panel) and paxillin (right panel) from NP-40 lysates of serum-starved U251 cells incubated with hPTN or hIL-34 (0.1 nM) western blotted with antibodies to phosphotyrosine (pY), FAK or Pax. (C) Abrogation of the IL-34 and PTN-induced phosphorylation of FAK and paxillin in U251 cells expressing PTP-ζ shRNA. Normalized to the total FAK and Pax expression and expressed as fold stimulation of levels in control (vehicle-treated) cells (dotted line).

To function as a receptor for IL-34, IL-34 binding to cell surface PTP-ζ should trigger intracellular signaling. Consistent with the reduction of PTP-ζ phosphatase activity by ligand binding (30,33,60), PTP-ζ ligand binding has previously been shown to trigger intracellular protein tyrosine phosphorylation (31,32,34,35). Following incubation of U251 cells with PTN or IL-34 for various times at 37° C., a similar ligand-induced tyrosine phosphorylation of proteins was observed, including those with apparent $M_r$s of ~190, ~125, ~120, ~70 and ~42 kDa, that peaked within the first 5 minutes of stimulation (FIG. 5A). PTP-ζ ligands have been shown to increase the tyrosine phosphorylation of FAK, in lung and prostate carcinomas and endothelial cells (31,37,40) and of paxillin, in osteoblastic cells (63). Either PTN or IL-34 also increased the tyrosine phosphorylation of FAK (~125 kDa) and paxillin (~70 kDa) in U251 cells (FIGS. 5 A, B). In contrast, there was no detectable increase in the tyrosine phosphorylation of the putative PTP-ζ substrates, β-catenin or β-adducin (32,34), in response to either ligand. IL-34-mediated activations of FAK and paxillin were abolished in the PTP-ζ-KD2 cell lines (FIG. 5C), demonstrating that tyrosine phosphorylation of these proteins, induced by IL-34, is mediated by PTP-ζ.

hIL-34 Binds to PTP-ζ in a Chondroitin Sulfate-Dependent Manner—

Figures 6A, 6B, 6C:
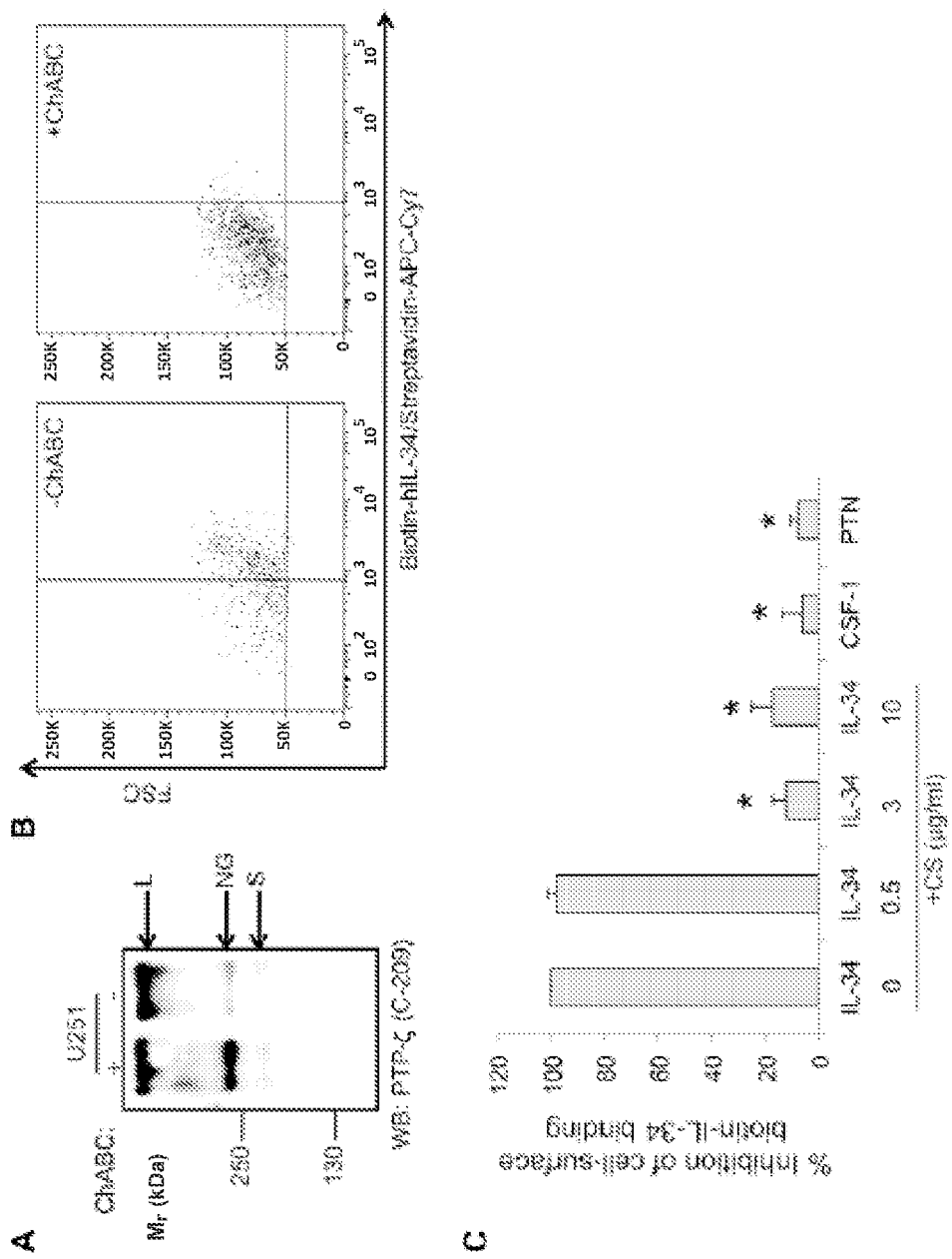
FIG. 6A-6C. IL-34 binds to PTP-ζ in a CS-dependent manner. (A) Effect of Chondroitinase ABC on specific PTP-ζ isoforms. Anti-PTP-ζ western blot of U251 membrane lysates incubated with and without chondroitinase ABC (0.3 U/ml, 37° C., 1 h). L, long isoform; NG, non-glycosaminoglycan isoform; S, short isoform. (B) CS is required for IL-34 binding to PTP-ζ. Serum-starved U251 cells were either incubated with, or without ChABC (4.2 Um') and subsequently with 2 μg/ml biotinylated hIL-34, prior to further incubation with streptavidin-conjugated APC-Cy7 and flow cytometric analysis, gating on viable cells. The vertical line defines the level of non-specific binding of biotinylated IL-34. (C) Competition with CS and the failure to compete with CSF-1 and PTN. $2 \times 10^5$ serum-starved U251 cells were pre-incubated with a 16 molar excess of IL-34 in the presence of increasing concentrations of CS, or with a 16 molar excess of CSF-1 or PTN, prior to washing and binding of biotinylated-IL-34 (2 μg/ml). Geometric means (G.M.) of signal intensities of duplicate experiments (average±range) were used to calculate percentage inhibition. *, p<0.05.

PTP-ζ is a proteoglycan receptor for several ligands (24-28) Furthermore, the PTP-ζ CS chains are known to affect binding to some of these ligands (25,29). The possible requirement of CS for IL-34 binding was therefore tested. Consistent with the previously reported presence of CS on PTP-ζ (19,64), treatment of solubilized U251 membranes with chondroitinase ABC increased the mobility of a significant fraction of the large PTP-ζ isoform (FIG. 6A). To determine the requirement of CS for cell surface binding, intact U251 cells were incubated with enzyme buffer alone, or with chondroitinase ABC, to remove cell surface CS. Treatment with chondroitinase ABC reduced binding of biotinylated IL-34 to the level seen in IL-34 competed cells (background levels) (FIG. 6B). Pre-incubation of U251 cells with a 16 molar excess of IL-34 blocked the subsequent binding of biotinylated IL-34, whereas pre-incubations with a 16 molar excess of CSF-1, or of PTN, were without effect (FIG. 6C). Consistent with the removal of binding sites by preincubation with chondroitinase ABC, pre-incubation of IL-34 with 3 μg/ml of shark cartilage CS blocked IL-34 inhibition of biotinylated IL-34 binding (FIG. 6C). Thus the CS GAG moiety of PTP-ζ is involved in IL-34 binding. SPR analysis further confirmed the inhibition by CS.

Comparative Expression Profiles of PTP-ζ, TN-R and IL-34 in Adult Brain—

Previous studies have shown that PTP-ζ is primarily expressed in neural progenitors and glial cells (21-23) as well as in a subset of cortical neurons (22,25). The expression of TN-R overlaps with PTP-ζ expression in rostral brain regions (77-79). IL-34 expression is primarily observed on mature neurons (9,16,76), including regions of the brain where PTP-ζ is expressed (23). IL-34 expression profiles are distinct from those of its cognate receptor, CSF-1R and also of CSF-1, and that it is preferentially increased in specific areas of early postnatal and adult forebrain, thereby suggesting the presence of an alternative signaling receptor (9). As PTP-ζ functions as a cell-surface receptor for IL-34 and also interacts with TN-R, the expression profiles of IL-34, PTP-ζ and TN-R were analyzed in 8-10 week-old mouse brains. PTP-ζ and TN-R were co-localized in OB, cerebral cortex, RMS and the CA3 region of the hippocampus that have previously been shown to express IL-34 (9). In addition, PTP-ζ expression remained prominent in distinct subcortical structures (thalamic and subthalamic nuclei), midbrain and brain stem nuclei (inferior colliculus, pontine nuclei, locus coeruleus and vestibular nuclei), as well as the cerebellum, and displayed distinct co-localization patterns with both IL-34 and TN-R. Mature post-mitotic neurons of the cerebrum were labeled by all three of these markers. These observations are consistent with a previous study that localized IL-34 expression preferentially to mature neurons of the adult cerebral cortex, extending from layers 2-5. In addition, IL-34 and PTP-ζ co-localization was particularly prominent in layer 5 of the cortex. Consistent with the existence of the secreted PTP-ζ isoform, PTP-ζ expression was also observed in the ECM of the cerebral cortex in concert with IL-34. IL-34 and PTP-ζ appeared to be uniformly distributed in the ECM of layer 5 and at the periphery of mature neuronal cell bodies. In contrast, in cortical layer 6, PTP-ζ expression was reduced in the ECM and neuronal soma, whereas IL-34 expression was virtually absent. Expression of TN-R was evident in cerebral cortical layers 2-5, most prominently in layer 4, where it was co-localized with IL-34 in both the ECM and at the periphery of mature neuronal somas. Its cellular and extra-cellular expression decreased in cortical layer 5. Finally, in contrast to the expression profiles of IL-34 and TN-R, PTP-ζ staining was also seen in GFAP+ adult neural stem cells present in the anterior SVZ, as well as in those neural species migrating through the RMS to the OB (21,23), but not in GFAP+ astrocytes in the CC.

Discussion

The differential and higher expression of IL-34, compared to CSF-1 and CSF-1R expression in brain coupled with the more pronounced effects of IL-34 compared with CSF-1 on neural progenitor cell self-renewal and differentiation (9,14), raised the possibility that IL-34 might signal via an alternate receptor. The present studies identified PTP-ζ, a cell-surface CSPG, as a second functional receptor for IL-34. IL-34 selectively interacts with PTP-ζ in membrane lysates from both mouse brain as well as U251 human glioblastoma cells. It binds to intact U251 cells, stimulates their phosphotyrosine signaling and suppresses their tumorigenic properties in a PTP-ζ-dependent manner. Furthermore, IL-34, but not CSF-1, binds PTP-ζ in vitro ($K_d$~10$^{-7}$M) and at the cell surface and whereas IL-34 and CSF-1 compete for binding to the CSF-1R (14,65,66), pre-incubation with a 16-molar excess of CSF-1 failed to compete for IL-34 binding to U251 cells. Thus PTP-ζ fulfills the criteria required for it to function as the postulated IL-34 receptor.

PTP-ζ is primarily expressed on neural progenitor and glial cells (21-23), as well as on a subset of cortical neurons (22,25). In contrast, IL-34 is expressed primarily on neurons (9,16) and also in the regions of the brain where PTP-ζ is expressed (23). Interestingly, IL-34 signaling via PTP-ζ in U251 glioblastoma cells causes a suppression of clonogenicity, similar to the effect of CSF-1 or IL-34 on isolated CSF-1R-expressing neural progenitors (9). This suppression of clonogenicity is correlated with stimulation of cellular tyrosine phosphorylation in either setting. Indeed, IL-34 was shown to be significantly more active in suppressing neural progenitor cell proliferation than CSF-1 (9), consistent with an additional action of IL-34 via the PTP-ζ receptor on the neural progenitor cells.

PTP-ζ-signaling plays a contrasting role in hematopoietic stem cells, leading to their expansion (67). A positive regulatory role of PTP-ζ in proliferation and migration was also reported in some glioblastomas (31,40), which could reflect the role of other known PTP-ζ co-receptors, such as the integrins β1 (63) and β3 (38), in governing these biological responses. Addition of IL-34 to U251 cells led to an increase in the tyrosine phosphorylation of FAK and paxillin and a suppression of cell motility. Although an increase in tyrosine phosphorylation of FAK is associated with an increase in proliferation and motility in other cells, it has been shown to inhibit these responses in glioblastomas (68). Also, similar to the present observations in U251 cells, increased tyrosine phosphorylation of paxillin is correlated with inhibition of motility in macrophages (69) and FAK (Y397) dephosphorylation promotes tumor metastasis (68). Thus, signaling via the PTP-ζ receptor can have contrasting biological effects in specific cellular contexts, possibly dependent on the differential expression of PTP-ζ co-receptors and the activation of specific signaling pathways.

In view of the striking dependence of the IL-34-PTP-ζ interaction on the CS GAG chain, it was of interest that IL-34 also bound to other CS and HS proteoglycans with low affinity. The CS inhibition of PTP-ζ binding and the finding that binding to brevican and glypican was effectively blocked by heparin, suggest that the low affinity binding of IL-34 to proteoglycans involves the electrostatic interactions between IL-34 and the proteoglycan GAG chains and that the nature of the GAG chain is the likely determinant of this interaction. This electrostatic interaction may also be an important part, but not the sole component, of the high affinity interaction of IL-34 with PTP-ζ and the reason for the CS inhibition that was observed.

Like IL-34, PTN also exhibits GAG-dependent binding to PTP-ζ. However, in contrast to IL-34, CS-C, but not shark cartilage CS, inhibits this binding (25). Furthermore, competition experiments showed that PTN fails to compete for the binding of IL-34 (FIG. 6C), suggesting that IL-34 binding could involve a different PTP-ζ CS GAG-moiety, not recognized by PTN. Interestingly, the CS-A replaces CS-C on the PTP-ζ receptor during development from embryonic to post-natal brain and this is correlated with a decrease in the expression of PTN (64,70). In contrast, IL-34 expression increases progressively during brain development (9).

The identification of PTP-ζ as a novel receptor for IL-34 necessitates a reevaluation of the possible role of IL-34/PTP-ζ signaling in tissues in which both ligand and receptor are expressed. Obviously the CNS is an important organ system because of the significant expression of both IL-34 and PTP-ζ in brain and because PTP-ζ has been implicated in several disease settings in the CNS. For example, it is expressed in remyelinating oligodendrocytes (OL) and PTP-ζ-deficient mice display a delayed recovery from demyelinating lesions in a model of experimental autoimmune encephalomyelitis (71). Furthermore, the soluble PTP-ζ isoform has been shown to be necessary for maturation for OL progenitors to differentiated myelin-secreting oligodendrocytes in vitro (72) and PTP-ζ-deficient mice exhibit increased myelin breakdown (73). In addition, PTPRZ1 gene in humans is a schizophrenia-susceptibility gene (74) and PTP-ζ regulates tyrosine phosphorylation of voltage-gated sodium channels in neurons (75). Given the present demonstration that IL-34 modulates tumorigenic properties of glioblastoma cell line U251, the fact that PTP-ζ is expressed in neuroblastomas (18) and other tumors (37,40), such as prostate and lung cancer, is highly relevant. IL-34 is also important for Langerhans cell development (16, 76), probably via RPTP-zeta.

REFERENCES

1. Sherr, C. J., Rettenmier, C. W., Sacca, R., Roussel, M. F., Look, A. T., and Stanley, E. R. (1985) The c-fms proto-oncogene product is related to the receptor for the mononuclear phagocyte growth factor, CSF-1. *Cell* 41, 665-676
2. Yeung, Y. G., Jubinsky, P. T., Sengupta, A., Yeung, D. C., and Stanley, E. R. (1987) Purification of the colony-stimulating factor 1 receptor and demonstration of its tyrosine kinase activity. *Proc Natl Acad Sci USA* 84, 1268-1271
3. Dai, X. M., Zong, X. H., Akhter, M. P., and Stanley, E. R. (2004) Osteoclast deficiency results in disorganized matrix, reduced mineralization, and abnormal osteoblast behavior in developing bone. *J Bone Miner Res* 19, 1441-1451
4. Yoshida, H., Hayashi, S., Kunisada, T., Ogawa, M., Nishikawa, S., Okamura, H., Sudo, T., Shultz, L. D., and Nishikawa, S. (1990) The murine mutation osteopetrosis is in the coding region of the macrophage colony stimulating factor gene. *Nature* 345, 442-444
5. Wiktor-Jedrzejczak, W., Bartocci, A., Ferrante, A. W., Jr., Ahmed-Ansari, A., Sell, K. W., Pollard, J. W., and Stanley, E. R. (1990) Total absence of colony-stimulating factor 1 in the macrophage-deficient osteopetrotic (op/op) mouse. *Proc Natl Acad Sci USA* 87, 4828-4832
6. Cecchini, M. G., Dominguez, M. G., Mocci, S., Wetterwald, A., Felix, R., Fleisch, H., Chisholm, O., Hofstetter, W., Pollard, J. W., and Stanley, E. R. (1994) Role of colony stimulating factor-1 in the establishment and regulation of tissue macrophages during postnatal development of the mouse. *Development* 120, 1357-1372
7. Huynh, D., Dai, X. M., Nandi, S., Lightowler, S., Trivett, M., Chan, C. K., Bertoncello, I., Ramsay, R. G., and Stanley, E. R. (2009) Colony stimulating factor-1 dependence of paneth cell development in the mouse small intestine. *Gastroenterology* 137, 136-144, 144 e131-133
8. Guleria, I., and Pollard, J. W. (2000) The trophoblast is a component of the innate immune system during pregnancy. *Nat Med* 6, 589-593
9. Nandi, S., Gokhan, S., Dai, X. M., Wei, S., Enikolopov, G., Lin, H., Mehler, M. F., and Stanley, E. R. (2012) The CSF-1 receptor ligands IL-34 and CSF-1 exhibit distinct developmental brain expression patterns and regulate neural progenitor cell maintenance and maturation. *Dev Biol* 367, 100-113
10. Pixley, F. J., and Stanley, E. R. (2004) CSF-1 regulation of the wandering macrophage: complexity in action. *Trends Cell Biol* 14, 628-638
11. Chitu, V., and Stanley, E. R. (2006) Colony-stimulating factor-1 in immunity and inflammation. *Curr Opin Immunol* 18, 39-48
12. Dai, X. M., Ryan, G. R., Hapel, A. J., Dominguez, M. G., Russell, R. G., Kapp, S., Sylvestre, V., and Stanley, E. R. (2002) Targeted disruption of the mouse colony-stimulating factor 1 receptor gene results in osteopetrosis, mononuclear phagocyte deficiency, increased primitive progenitor cell frequencies, and reproductive defects. *Blood* 99, 111-120
13. Lin, H., Lee, E., Hestir, K., Leo, C., Huang, M., Bosch, E., Halenbeck, R., Wu, G., Zhou, A., Behrens, D., Hollenbaugh, D., Linnemann, T., Qin, M., Wong, J., Chu, K., Doberstein, S. K., and Williams, L. T. (2008) Discovery of a cytokine and its receptor by functional screening of the extracellular proteome. *Science* 320, 807-811
14. Wei, S., Nandi, S., Chitu, V., Yeung, Y. G., Yu, W., Huang, M., Williams, L. T., Lin, H., and Stanley, E. R. (2010) Functional overlap but differential expression of CSF-1 and IL-34 in their CSF-1 receptor-mediated regulation of myeloid cells. *J Leukoc Biol* 88, 495-505
15. Ginhoux, F., Greter, M., Leboeuf, M., Nandi, S., See, P., Gokhan, S., Mehler, M. F., Conway, S. J., Ng, L. G., Stanley, E. R., Samokhvalov, I. M., and Merad, M. (2010) Fate mapping analysis reveals that adult microglia derive from primitive macrophages. *Science* 330, 841-845
16. Wang, Y., Szretter, K. J., Vermi, W., Gilfillan, S., Rossini, C., Cella, M., Barrow, A. D., Diamond, M. S., Colonna, M. (2012) IL-34 is a tissue-restricted ligand of CSF1R required for the development of Langerhans cells and microglia. *Nat Immunol* 13, 753-760
17. Chihara, T., Suzu, S., Hassan, R., Chutiwitoonchai, N., Hiyoshi, M., Motoyoshi, K., Kimura, F., and Okada, S. (2010) IL-34 and M-CSF share the receptor Fms but are not identical in biological activity and signal activation. *Cell Death Differ* 17, 1917-1927
18. Levy, J. B., Canoll, P. D., Silvennoinen, O., Barnea, G., Morse, B., Honegger, A. M., Huang, J. T., Cannizzaro, L. A., Park, S. H., Druck, T., and et al. (1993) The cloning of a receptor-type protein tyrosine phosphatase expressed in the central nervous system. *J Biol Chem* 268, 10573-10581
19. Barnea, G., Grumet, M., Miley, P., Silvennoinen, O., Levy, J. B., Sap, J., and Schlessinger, J. (1994) Receptor tyrosine phosphatase beta is expressed in the form of proteoglycan and binds to the extracellular matrix protein tenascin. *J Biol Chem* 269, 14349-14352
20. Krueger, N. X., and Saito, H. (1992) A human transmembrane protein-tyrosine-phosphatase, PTP zeta, is expressed in brain and has an N-terminal receptor domain homologous to carbonic anhydrases. *Proc Natl Acad Sci USA* 89, 7417-7421
21. von Holst, A., Sirko, S., and Faissner, A. (2006) The unique 473HD-Chondroitinsulfate epitope is expressed by radial glia and involved in neural precursor cell proliferation. *J Neurosci* 26, 4082-4094
22. Shintani, T., Watanabe, E., Maeda, N., and Noda, M. (1998) Neurons as well as astrocytes express proteoglycan-type protein tyrosine phosphatase zeta/RPTPbeta: analysis of mice in which the PTPzeta/RPTPbeta gene was replaced with the LacZ gene. *Neurosci Lett* 247, 135-138
23. Lafont, D., Adage, T., Greco, B., and Zaratin, P. (2009) A novel role for receptor like protein tyrosine phosphatase zeta in modulation of sensorimotor responses to noxious stimuli: evidences from knockout mice studies. *Behav Brain Res* 201, 29-40
24. Peles, E., Schlessinger, J., and Grumet, M. (1998) Multi-ligand interactions with receptor-like protein tyrosine phosphatase beta: implications for intercellular signaling. *Trends Biochem Sci* 23, 121-124
25. Maeda, N., Nishiwaki, T., Shintani, T., Hamanaka, H., and Noda, M. (1996) 6B4 proteoglycan/phosphacan, an extracellular variant of receptor-like protein-tyrosine phosphatase zeta/RPTPbeta, binds pleiotrophin/heparin-binding growth-associated molecule (HB-GAM). *J Biol Chem* 271, 21446-21452
26. Li, Y. S., Milner, P. G., Chauhan, A. K., Watson, M. A., Hoffman, R. M., Kodner, C. M., Milbrandt, J., and Deuel, T. F. (1990) Cloning and expression of a developmentally regulated protein that induces mitogenic and neurite outgrowth activity. *Science* 250, 1690-1694
27. Peles, E., Nativ, M., Campbell, P. L., Sakurai, T., Martinez, R., Lev, S., Clary, D. O., Schilling, J., Barnea, G., Plowman, G. D., Grumet, M., and Schlessinger, J. (1995) The carbonic anhydrase domain of receptor tyrosine phosphatase beta is a functional ligand for the axonal cell recognition molecule contactin. *Cell* 82, 251-260
28. Miley, P., Chiba, A., Haring, M., Rauvala, H., Schachner, M., Ranscht, B., Margolis, R. K., and Margolis, R. U. (1998) High affinity binding and overlapping localization of neurocan and phosphacan/protein-tyrosine phosphatase-zeta/beta with tenascin-R, amphoterin, and the heparin-binding growth-associated molecule. *J Biol Chem* 273, 6998-7005
29. Maeda, N., Ichihara-Tanaka, K., Kimura, T., Kadomatsu, K., Muramatsu, T., and Noda, M. (1999) A receptor-like protein-tyrosine phosphatase PTPzeta/RPTPbeta binds a heparin-binding growth factor midkine. Involvement of arginine 78 of midkine in the high affinity binding to PTPzeta. *J Biol Chem* 274, 12474-12479
30. Majeti, R., Bilwes, A. M., Noel, J. P., Hunter, T., and Weiss, A. (1998) Dimerization-induced inhibition of receptor protein tyrosine phosphatase function through an inhibitory wedge. *Science* 279, 88-91
31. Polykratis, A., Katsoris, P., Courty, J., and Papadimitriou, E. (2005) Characterization of heparin affin regulatory peptide signaling in human endothelial cells. *J Biol Chem* 280, 22454-22461

32. Meng, K., Rodriguez-Pena, A., Dimitrov, T., Chen, W., Yamin, M., Noda, M., and Deuel, T. F. (2000) Pleiotrophin signals increased tyrosine phosphorylation of beta beta-catenin through inactivation of the intrinsic catalytic activity of the receptor-type protein tyrosine phosphatase beta/zeta. *Proc Natl Acad Sci USA* 97, 2603-2608

33. Fukada, M., Fujikawa, A., Chow, J. P., Ikematsu, S., Sakuma, S., and Noda, M. (2006) Protein tyrosine phosphatase receptor type Z is inactivated by ligand-induced oligomerization. *FEBS Lett* 580, 4051-4056

34. Pariser, H., Perez-Pinera, P., Ezquerra, L., Herradon, G., and Deuel, T. F. (2005) Pleiotrophin stimulates tyrosine phosphorylation of beta-adducin through inactivation of the transmembrane receptor protein tyrosine phosphatase beta/zeta. *Biochem Biophys Res Commun* 335, 232-239

35. Pariser, H., Ezquerra, L., Herradon, G., Perez-Pinera, P., and Deuel, T. F. (2005) Fyn is a downstream target of the pleiotrophin/receptor protein tyrosine phosphatase beta/zeta-signaling pathway: regulation of tyrosine phosphorylation of Fyn by pleiotrophin. *Biochem Biophys Res Commun* 332, 664-669

36. Fujikawa, A., Fukada, M., Makioka, Y., Suzuki, R., Chow, J. P., Matsumoto, M., and Noda, M. (2011) Consensus substrate sequence for protein-tyrosine phosphatase receptor type Z. *J Biol Chem* 286, 37137-37146

37. Diamantopoulou, Z., Kitsou, P., Menashi, S., Courty, J., and Katsoris, P. (2012) Loss of Receptor Protein Tyrosine Phosphatase beta/zeta (RPTPbeta/zeta) Promotes Prostate Cancer Metastasis. *J Biol Chem* 287, 40339-40349

38. Mikelis, C., Sfaelou, E., Koutsioumpa, M., Kieffer, N., and Papadimitriou, E. (2009) Integrin alpha(v)beta(3) is a pleiotrophin receptor required for pleiotrophin-induced endothelial cell migration through receptor protein tyrosine phosphatase beta/zeta. *Faseb J* 23, 1459-1469

39. Muller, S., Kunkel, P., Lamszus, K., Ulbricht, U., Lorente, G. A., Nelson, A. M., von Schack, D., Chin, D. J., Lohr, S. C., Westphal, M., and Melcher, T. (2003) A role for receptor tyrosine phosphatase zeta in glioma cell migration. *Oncogene* 22, 6661-6668

40. Feng, Z. J., Gao, S. B., Wu, Y., Xu, X. F., Hua, X., and Jin, G. H. (2010) Lung cancer cell migration is regulated via repressing growth factor PTN/RPTP beta/zeta signaling by menin. *Oncogene* 29, 5416-5426

41. Yu, W., Chen, J., Xiong, Y., Pixley, F. J., Yeung, Y. G., and Stanley, E. R. (2012) Macrophage proliferation is regulated through CSF-1 receptor tyrosines 544, 559, and 807. *J Biol Chem* 287, 13694-13704

42. Garwood, J., Schnadelbach, O., Clement, A., Schutte, K., Bach, A., and Faissner, A. (1999) DSD-1-proteoglycan is the mouse homolog of phosphacan and displays opposing effects on neurite outgrowth dependent on neuronal lineage. *J Neurosci* 19, 3888-3899

43. Edmonds, B. T., Wyckoff, J., Yeung, Y. G., Wang, Y., Stanley, E. R., Jones, J., Segall, J., and Condeelis, J. (1996) Elongation factor-1 alpha is an overexpressed actin binding protein in metastatic rat mammary adenocarcinoma. *J Cell Sci* 109 (Pt 11), 2705-2714

44. Yeung, Y. G., Nieves, E., Angeletti, R. H., Stanley, E. R. (2008) Removal of detergents from protein digests for mass spectrometry analysis. *Anal Biochem* 382, 135-137

45. Yeung, Y. G., Stanley, E. R. (2003) Proteomic approaches to the analysis of early events in colony-stimulating factor-1 signal transduction. *Mol Cell Proteomics* 2, 1143-1155

46. Roussel, M. F., Dull, T. J., Rettenmier, C. W., Ralph, P., Ullrich, A., and Sherr, C. J. (1987) Transforming potential of the c-fms proto-oncogene (CSF-1 receptor). *Nature* 325, 549-552

47. Morgan, C., Pollard, J. W., and Stanley, E. R. (1987) Isolation and characterization of a cloned growth factor dependent macrophage cell line, BAC1.2F5. *J Cell Physiol* 130, 420-427

48. Li, W, Stanley, ER. (1991) Role of dimerization and modification of the CSF-1 receptor in its activation and internalization during the CSF-1 response. *Embo J* 10, 277-88

49. Nishiwaki, T., Maeda, N., and Noda, M. (1998) Characterization and developmental regulation of proteoglycan-type protein tyrosine phosphatase zeta/RPTPbeta isoforms. *J Biochem* 123, 458-467

50. Sakurai, T., Friedlander, D. R., and Grumet, M. (1996) Expression of polypeptide variants of receptor-type protein tyrosine phosphatase beta: the secreted form, phosphacan, increases dramatically during embryonic development and modulates glial cell behavior in vitro. *J Neurosci Res* 43, 694-706

51. Chow, J. P., Fujikawa, A., Shimizu, H., Suzuki, R., and Noda, M. (2008) Metalloproteinase- and gamma-secretase-mediated cleavage of protein-tyrosine phosphatase receptor type Z. *J Biol Chem* 283, 30879-30889

52. Woodworth, A., Pesheva, P., Fiete, D., and Baenziger, J. U. (2004) Neuronal-specific synthesis and glycosylation of tenascin-R. *J Biol Chem* 279, 10413-10421

53. Maurel, P., Rauch, U., Flad, M., Margolis, R. K., and Margolis, R. U. (1994) Phosphacan, a chondroitin sulfate proteoglycan of brain that interacts with neurons and neural cell-adhesion molecules, is an extracellular variant of a receptor-type protein tyrosine phosphatase. *Proc Natl Acad Sci USA* 91, 2512-2516

54. Xiao, Z. C., Bartsch, U., Margolis, R. K., Rougon, G., Montag, D., and Schachner, M. (1997) Isolation of a tenascin-R binding protein from mouse brain membranes. A phosphacan-related chondroitin sulfate proteoglycan. *J Biol Chem* 272, 32092-32101

55. shiara, K., Yamada, H., Watanabe, K., Shimonaka, M., and Yamaguchi, Y. (1994) Brain-specific receptor-type protein-tyrosine phosphatase RPTP beta is a chondroitin sulfate proteoglycan in vivo. *J Biol Chem* 269, 20189-20193

56. Maeda, N., and Noda, M. (1998) Involvement of receptor-like protein tyrosine phosphatase zeta/RPTPbeta and its ligand pleiotrophin/heparin-binding growth-associated molecule (HB-GAM) in neuronal migration. *J Cell Biol* 142, 203-216

57. Fukazawa, N., Yokoyama, S., Eiraku, M., Kengaku, M., and Maeda, N. (2008) Receptor type protein tyrosine phosphatase zeta-pleiotrophin signaling controls endocytic trafficking of DNER that regulates neuritogenesis. *Mol Cell Biol* 28, 4494-4506

58. Ulbricht, U., Eckerich, C., Fillbrandt, R., Westphal, M., and Lamszus, K. (2006) RNA interference targeting protein tyrosine phosphatase zeta/receptor-type protein tyrosine phosphatase beta suppresses glioblastoma growth in vitro and in vivo. *J Neurochem* 98, 1497-1506

59. Foehr, E. D., Lorente, G., Kuo, J., Ram, R., Nikolich, K., and Urfer, R. (2006) Targeting of the receptor protein tyrosine phosphatase beta with a monoclonal antibody delays tumor growth in a glioblastoma model. *Cancer Res* 66, 2271-2278

60. Barr, A. J., Ugochukwu, E., Lee, W. H., King, O. N., Filippakopoulos, P., Alfano, I., Savitsky, P., Burgess- Brown, N. A., Muller, S., Knapp, S. (2009) Large-scale structural analysis of the classical human protein tyrosine phosphatome. *Cell* 136, 352-363

61. Lu, K. V., Jong, K. A., Kim, G. Y., Singh, J., Dia, E. Q., Yoshimoto, K., Wang, M. Y., Cloughesy, T. F., Nelson, S. F., and Mischel, P. S. (2005) Differential induction of glioblastoma migration and growth by two forms of pleiotrophin. *J Biol Chem* 280, 26953-26964

62. Qi, M., Ikematsu, S., Maeda, N., Ichihara-Tanaka, K., Sakuma, S., Noda, M., Muramatsu, T., and Kadomatsu, K. (2001) Haptotactic migration induced by midkine. Involvement of protein-tyrosine phosphatase zeta. Mitogen-activated protein kinase, and phosphatidylinositol 3-kinase. *J Biol Chem* 276, 15868-15875

63. Muramatsu, H., Zou, P., Suzuki, H., Oda, Y., Chen, G. Y., Sakaguchi, N., Sakuma, S., Maeda, N., Noda, M., Takada, Y., and Muramatsu, T. (2004) alpha4beta1- and alpha6beta1-integrins are functional receptors for midkine, a heparin-binding growth factor. *J Cell Sci* 117, 5405-5415

64. Maeda, N., Hamanaka, H., Oohira, A., and Noda, M. (1995) Purification, characterization and developmental expression of a brain-specific chondroitin sulfate proteoglycan, 6B4 proteoglycan/phosphacan. *Neuroscience* 67, 23-35

65. Ma, X., Lin, W. Y., Chen, Y., Stawicki, S., Mukhyala, K., Wu, Y., Martin, F., Bazan, J. F., and Starovasnik, M. A. (2012) Structural basis for the dual recognition of helical cytokines IL-34 and CSF-1 by CSF-1R. *Structure* 20, 676-687

66. Liu, H., Leo, C., Chen, X., Wong, B. R., Williams, L. T., Lin, H., and He, X. (2012) The mechanism of shared but distinct CSF-1R signaling by the non-homologous cytokines IL-34 and CSF-1. *Biochim Biophys Acta* 1824, 938-945

67. Himburg, H. A., Muramoto, G. G., Daher, P., Meadows, S. K., Russell, J. L., Doan, P., Chi, J. T., Salter, A. B., Lento, W. E., Reya, T., Chao, N. J., and Chute, J. P. (2010) Pleiotrophin regulates the expansion and regeneration of hematopoietic stem cells. *Nat Med* 16, 475-482

68. Zheng, Y., Xia, Y., Hawke, D., Halle, M., Tremblay, M. L., Gao, X., Zhou, X. Z., Aldape, K., Cobb, M. H., Xie, K., He, J., and Lu, Z. (2009) FAK phosphorylation by ERK primes ras-induced tyrosine dephosphorylation of FAK mediated by PIN1 and PTP-PEST. *Mol Cell* 35, 11-25

69. Pixley, F. J., Lee, P. S., Condeelis, J. S., and Stanley, E. R. (2001) Protein tyrosine phosphatase phi regulates paxillin tyrosine phosphorylation and mediates colony-stimulating factor 1-induced morphological changes in macrophages. *Mol Cell Biol* 21, 1795-1809

70. Rauch, U., Gao, P., Janetzko, A., Flaccus, A., Hilgenberg, L., Tekotte, H., Margolis, R. K., and Margolis, R. U. (1991) Isolation and characterization of developmentally regulated chondroitin sulfate and chondroitin/keratan sulfate proteoglycans of brain identified with monoclonal antibodies. *J Biol Chem* 266, 14785-14801

71. Harroch, S., Furtado, G. C., Brueck, W., Rosenbluth, J., Lafaille, J., Chao, M., Buxbaum, J. D., and Schlessinger, J. (2002) A critical role for the protein tyrosine phosphatase receptor type Z in functional recovery from demyelinating lesions. *Nat Genet* 32, 411-14

72. Lamprianou, S., Chatzopoulou, E., Thomas, J. L., Bouyain, S., and Harroch, S. (2011) A complex between contactin-1 and the protein tyrosine phosphatase PTPRZ controls the development of oligodendrocyte precursor cells. *Proc Natl Acad Sci USA* 108, 17498-17503

73. Harroch, S., Palmeri, M., Rosenbluth, J., Custer, A., Okigaki, M., Shrager, P., Blum, M., Buxbaum, J. D., and Schlessinger, J. (2000) No obvious abnormality in mice deficient in receptor protein tyrosine phosphatase beta. *Mol Cell Biol* 20, 7706-7715

74. Buxbaum, J. D., Georgieva, L., Young, J. J., Plescia, C., Kajiwara, Y., Jiang, Y., Moskvina, V., Norton, N., Peirce, T., Williams, H., Craddock, N. J., Carroll, L., Corfas, G., Davis, K. L., Owen, M. J., Harroch, S., Sakurai, T., and O'Donovan, M. C. (2008) Molecular dissection of NRG1-ERBB4 signaling implicates PTPRZ1 as a potential schizophrenia susceptibility gene. *Mol Psychiatry* 13, 162-172

75. Ratcliffe, C. F., Qu, Y., McCormick, K. A., Tibbs, V. C., Dixon, J. E., Scheuer, T., and Catterall, W. A. (2000) A sodium channel signaling complex: modulation by associated receptor protein tyrosine phosphatase beta. *Nat Neurosci* 3, 437-444.

76. Greter, M., Lelios, I., Pelczar, P., Hoeffel, G., Price, J., Leboeuf, M., Kundig, T. M., Frei, K., Ginhoux, F., Merad, M., and Becher, B. (2012) Stroma-derived interleukin-34 controls the development and maintenance of langerhans cells and the maintenance of microglia. *Immunity* 37, 1050-1060.

77. El Ayachi, I., Fernandez, C., Baeza, N., De Paula, A. M., Pesheva, P., and Figarella-Branger, D. (2011) Spatiotemporal distribution of tenascin-R in the developing human cerebral cortex parallels neuronal migration. *J Comp Neurol* 519, 2379-2389.

78. Saghatelyan, A., de Chevigny, A., Schachner, M., and Lledo, P. M. (2004) Tenascin-R mediates activity-dependent recruitment of neuroblasts in the adult mouse forebrain. *Nat Neurosci* 7, 347-356.

79. Woodworth, A., Fiete, D., and Baenziger, J. U. (2002) Spatial and temporal regulation of tenascin-R glycosylation in the cerebellum. *J Biol Chem* 277, 50941-50947.

What is claimed is:

1. A method for determining whether or not an agent is a candidate agent for inhibiting interaction between interleukin-34 (IL-34) and protein tyrosine phosphatase receptor type zeta (PTP-ζ) comprising:
   contacting cells that express PTP-ζ on their surface and that do not express colony stimulating factor-1 receptor (CSF-1R) with IL-34 in the presence of the agent and in the absence of the agent, and
   measuring a cellular response induced by IL-34,
   wherein an agent that reduces a cellular response induced by IL-34 is a candidate agent for inhibiting interaction between IL-34 and PTP-ζ, and
   wherein an agent that does not reduce a cellular response induced by IL-34 is not a candidate agent for inhibiting interaction between IL-34 and PTP-ζ.

2. The method of claim 1, wherein the cells are glioblastoma cells.

3. The method of claim 1, wherein the cells are U251 human glioblastoma cells.

4. The method of claim 1, wherein the cells have been transfected with nucleic acid encoding human PTP-ζ.

5. The method of claim 1, wherein IL-34 inhibits one or more of cell proliferation, clonogenicity and/or motility.

6. The method of claim 1, wherein IL-34 induces tyrosine phosphorylation of a protein.

7. The method of claim 6, wherein IL-34-induces tyrosine phosphorylation of focal adhesion kinase (FAK) and/or paxillin.

8. The method of claim 1, wherein IL-34 stimulates differentiation of neural progenitor cells.

9. The method of claim 1, wherein the agent binds to a chondroitin sulfate glycosaminoglycan (GAG) moiety on PTP-ζ.

* * * * *

UNITED STATES PATENT AND TRADEMARK OFFICE
CERTIFICATE OF CORRECTION

PATENT NO. : 9,671,391 B2
APPLICATION NO. : 14/891405
DATED : June 6, 2017
INVENTOR(S) : Evan Richard Stanely et al.

Page 1 of 1

It is certified that error appears in the above-identified patent and that said Letters Patent is hereby corrected as shown below:

In the Specification

In Column 1, at Line 16, "This invention was made with government support under grant numbers CA032551, CA013330 and RR019352 awarded by the National Institutes of Health. The government has certain rights in the invention." should read --This invention was made with government support under grant numbers CA032551 and CA013330 awarded by the National Institutes of Health. The government has certain rights in the invention.--

Signed and Sealed this
Twelfth Day of February, 2019

Andrei Iancu
*Director of the United States Patent and Trademark Office*